(12) United States Patent
Vasudevan et al.

(10) Patent No.: US 7,998,982 B2
(45) Date of Patent: Aug. 16, 2011

(54) AMIDE DERIVATIVES AS TRPV1 ANTAGONISTS

(75) Inventors: Anil Vasudevan, Union Grove, WI (US); Brian S. Brown, Evanston, IL (US); Jerome F. Daanen, Racine, WI (US); Arthur R. Gomtsyan, Vernon Hills, IL (US); Tammie K. Jinkerson, Pleasant Prairie, WI (US); Ryan G. Keddy, Beach Park, IL (US); Michael E. Kort, Lake Bluff, IL (US); Philip R. Kym, Libertyville, IL (US); Mark A. Matulenko, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 12/188,323

(22) Filed: Aug. 8, 2008

(65) Prior Publication Data

US 2009/0062345 A1    Mar. 5, 2009

Related U.S. Application Data

(60) Provisional application No. 60/954,945, filed on Aug. 9, 2007.

(51) Int. Cl.
*A61K 31/4412* (2006.01)
*C07D 213/22* (2006.01)
(52) U.S. Cl. ......................... 514/334; 546/257
(58) Field of Classification Search ................... 546/194, 546/257; 514/318, 334
See application file for complete search history.

(56) References Cited

U.S. PATENT DOCUMENTS

| 7,129,235 B2 | 10/2006 | Zheng et al. |
| 2005/0080095 A1 | 4/2005 | Zheng et al. |
| 2006/0128755 A1 | 6/2006 | Nakagawa et al. |

FOREIGN PATENT DOCUMENTS

| EP | 1627869 A1 | 2/2006 |
| WO | WO2005004866 A1 | 1/2005 |
| WO | WO 2005004866 | * 12/2005 |

OTHER PUBLICATIONS

Zcaplus 2005:55064, "Preparation of substituted cyclo (hetero) alkenes for treating pain", Kyle et. al., Dec. 2005.*
Fessenden et. al., Organic Chemistry, 4th Edition, 1990, pp. 156, 815.*
Karrer, Org. Chem., 2nd Ed., pp. 92-102 (1946).*
Caterina et al., "Impaired Nociception and Pain Sensation in Mice Lacking the Capsaicin Receptor," Science, 2000, 306-313, vol. 288.
Caterina M.J. et al., "The Capsaicin Receptor: A Heat-Activated Ion Channel in the Pain Pathway," (Binary/Image), 1997, 816-824, vol. 389.

Davis et al., "Vanilloid receptor-1 is essential for inflammatory thermal hyperalgesia," (Binary/Image), 2000, 183-187, vol. 405.
Fernihough J., Gentry C., Bevan S., Winter J., "Regulation of calcitonin gene-related peptide and TRPV1 in a rat model of osteoarthritis," Neurosci Lett, 2005, 75-80, 0388-02-01.
Fowler, C. "Intravesical Treatment of Overactive Bladder," Urology, 2000, 60-64, vol. 55.
Geppetti P., Materazzi S., Nicoletti P., "The transient receptor potential vanilloid 1: role in airway inflmmation and disease," Eur J Pharmacol, 2006, 207-14, 0533-01-03.
Grennan D.M., Jayson M.I.V., "Rheumatoid arthritis", Textbook of Pain, 1994, 397-407.
Higuchi T. and Stella V. (Editors). "Pro-Drugs as Novel Delivery Systems," ACS Symposium Series, 1975, vol. 14.
Hogue J.H., Mersfelder T.L., "Pathophysiology and first-line treatment of osteoarthritis," Ann Pharmacother, 2002, 679-86, 36/4.
Honore P., Wismer C.T., Mikusa J., et al., "A-425619 [1-lsoquinolin-5-yl-3-(4-trifluoromethyl-benzyl)-urea], a Novel Transient Receptor Potential Type V1 Receptor Antagonist, Relieves Pathophysiological Pain Associated with Inflammation and Tissue Injury in Rats," J Pharmacol Exp Thera, 2005, 410-421, 314.
International Search Report for application No. PCT/US08/072560, Mailed on Jan. 29, 2009, 2 pages.
Jia Y., McLeod R.L., Wang X., et al., "Anandamide induces cough in conscious guinea-pigs through VR1 receptors," Br J Pharmacol, 2002, 0831-06-01, 0137-06-01.
Levine, Ion et.al., "Inflammatory pain," Textbook of Pain, pp. 45-56.
Marsch R, Foeller E, Rammes G, et al., "Reduced anxiety, conditioned fear, and hippocampal long-term potentiation in transient receptor potential vanilloid type 1 receptor-deficient mice," J Neurosci, 2007, 0832-09-01, 27/4.
McCarthy C., "Osteoarthritis," Textbook of Pain, pp. 387-396.
Meyer A. Richard et al., "Peripheral neural mechanisms of nociception," Textbook of Pain, pp. 13-44.
Millan MJ, "The induction of pain: an integrative review," Prog Neurobiol, 1999, 0164-01-01, 57/1.
Nolano et al., "Topical Capsaicin in Humans: Parallel Loss of Epidermal Nerve Fibers and Pain Sensation," (Binary/Image), 1999, 135-145, vol. 81.

(Continued)

*Primary Examiner* — Taofiq A Solola
(74) *Attorney, Agent, or Firm* — Lisa V. Mueller; Polsinelli Shughart PC

(57) ABSTRACT

The present invention relates to compounds of formula (I), or pharmaceutically acceptable salts, prodrugs, salts of prodrugs, or combinations thereof,

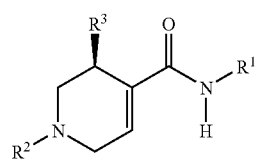

wherein $R^1$, $R^2$, and $R^3$, are defined in the specification. Compositions comprising such compounds and methods for treating conditions and disorders using such compounds and compositions are also disclosed.

6 Claims, No Drawings

OTHER PUBLICATIONS

Prescott, et al., "Lipid Vesicles as Carriers for Introducing Biologically Active Materials into Cells," Methods in Cell Biology, 1976, 33-71, vol. 14, Academic Press.

Roche E.B., (Editor). "Bioreversible Carriers in Drug Design," American Pharmaceutical Association, 1987, Pergamon Press.

Suni A., Szallasi A., "The emerging role of TRPV1 in diabetes and obesity," Trends in Pharmacology, 2008, 29-36, 29/1.

Szallasi A., Cortright D.N., Blum C.A., et al., "The vanilloid receptor TRPV1: 10 years from channel cloning to antagonist proof-of-concept," Nature Reviews, Drug Discovery, 2007, 357-372, 6.

Tzavara ET, Li DL, Moutsimilli L, et al., "Endocannabinoids activate transient receptor potential vanilloid 1 receptors to reduce hyperdoaminergia-related hyperactivity: therapeutic implications," Biol Psychiatry, 2006, 508-15, 59/6.

Watanabe N., Horie S., Michael G.J., et al., "Immunohistochemical localization of vanilloid receptor subtype 1 (TRPV1) in the guinea pig respiratory system," Pulm Pharmacol Ther, 2005, 187-97, 18/3.

Woolf C.J., Decosterd I, "Implications of recent advances in the understanding of pain pathophysiology for the assessment of pain in patients," Pain, 1999, S141-7, Suppl 6.

Woolf C.J., et al., "Neuronal Plasticity: Increasing the Gain in Pain," Science, 2000, 1765-1768, 288.

Woolf C.J., Mannion R.J., "Neuropathic pain: aetiology, symptoms, mechanisms, and management," Lancet, 1999, 1959-1964, 353.

* cited by examiner

AMIDE DERIVATIVES AS TRPV1 ANTAGONISTS

This application claims priority to U.S. Ser. No. 60/954,945 filed Aug. 9, 2007, and is incorporated herein by reference, in its entirety.

TECHNICAL FIELD

The present invention relates to (3S)-3-alkyl-3,6-dihydro-2H-pyridine-4-carboxamide enantiomers which are useful for useful for treating pain, bladder overactivity, or urinary incontinence. Pharmaceutical compositions comprising compounds of the invention and methods for treating pain, bladder overactivity, or urinary incontinence are also included.

BACKGROUND

Nociceptors are primary sensory afferent (C and Aδ fibers) neurons that are activated by a wide variety of noxious stimuli including chemical, mechanical, thermal, and proton (pH<6) modalities. The lipophillic vanilloid, capsaicin, activates primary sensory fibers via a specific cell surface capsaicin receptor, cloned as the transient receptor potential vanilloid-1 (TRPV1). TRPV1 is also known as vanilloid receptor-1 (VR1). The intradermal administration of capsaicin is characterized by an initial burning or hot sensation followed by a prolonged period of analgesia. The analgesic component of the TRPV1 receptor activation is thought to be mediated by a capsaicin-induced desensitization of the primary sensory afferent terminal. Thus, the long lasting anti-nociceptive effect of capsaicin has prompted the clinical use of capsaicin analogs as analgesic agents. Further, capsazepine, a capsaicin receptor antagonist can reduce inflammation-induced hyperalgesia in animal models. TRPV1 receptors are also localized on sensory afferents, which innervate the bladder. Capsaicin or resiniferatoxin has been shown to ameliorate incontinence symptoms upon injection into the bladder.

The TRPV1 receptor has been called a "polymodal detector" of noxious stimuli since it can be activated in several ways. The receptor channel is activated by capsaicin and other vanilloids, and thus is classified as a ligand-gated ion channel. The TRPV1 receptor activation by capsaicin can be blocked by the competitive TRPV1 receptor antagonist, capsazepine. The channel can also be activated by protons. Under mildly acidic conditions (pH 6-7), the affinity of capsaicin for the receptor is increased, whereas at pH<6, direct activation of the channel occurs. In addition, when membrane temperature reaches 43° C., the channel is opened. Thus heat can directly gate the channel in the absence of ligand. The capsaicin analog, capsazepine, which is a competitive antagonist of capsaicin, blocks activation of the channel in response to capsaicin, acid, or heat.

The channel is a nonspecific cation conductor. Both extracellular sodium and calcium enter through the channel pore, resulting in cell membrane depolarization. This depolarization increases neuronal excitability, leading to action potential firing and transmission of a noxious nerve impulse to the spinal cord. In addition, depolarization of the peripheral terminal can lead to release of inflammatory peptides such as, but not limited to, substance P and CGRP, leading to enhanced peripheral sensitization of tissue.

Recently, two groups have reported the generation of a "knock-out" mouse lacking the TRPV1 receptor. Electrophysiological studies of sensory neurons (dorsal root ganglia) from these animals revealed a marked absence of responses evoked by noxious stimuli including capsaicin, heat, and reduced pH. These animals did not display any overt signs of behavioral impairment and showed no differences in responses to acute non-noxious thermal and mechanical stimulation relative to wild-type mice. The TRPV1 (−/−) mice also did not show reduced sensitivity to nerve injury-induced mechanical or thermal nociception. However, the TRPV1 knock-out mice were insensitive to the noxious effects of intradermal capsaicin, exposure to intense heat (50-55° C.), and failed to develop thermal hyperalgesia following the intradermal administration of carrageenan.

U.S. Pat. No. 7,129,235 describes compounds of formula (a) that are vanilloid receptor antagonists and are useful in treating pain

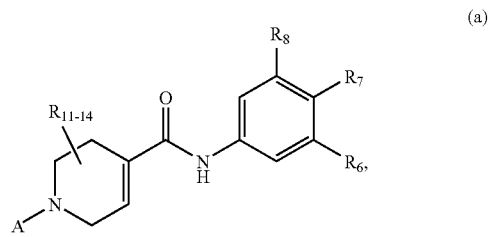

(a)

wherein A is pyridinyl, phenyl, thiazolyl, oxazolyl, imidazolyl, etc., $R_{11-14}$ are hydrogen, alkoxy, alkyl, or hydroxy, $R_6$, $R_7$, and $R_8$ are hydrogen, alkyl, haloalkyl, and the like.

U.S. Application publication No. 2006/0128755 discloses compounds of formulae (b) and (c) that exhibit anti-inflammatory and analgesic activities

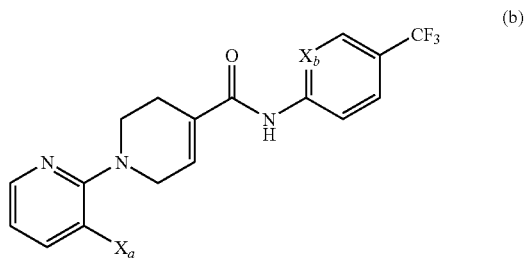

(b)

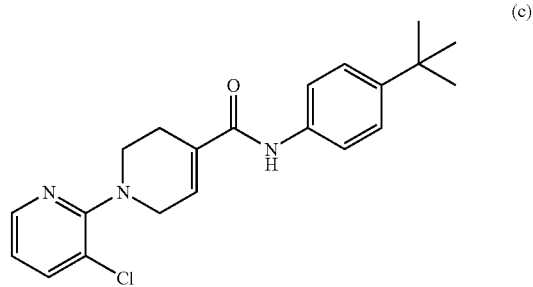

(c)

wherein $X_a$ is Cl or $CF_3$, and $X_b$ is N or CH.

In addition, a cyclo(hetero)alkenyl compound of formula (d) has been disclosed in publication

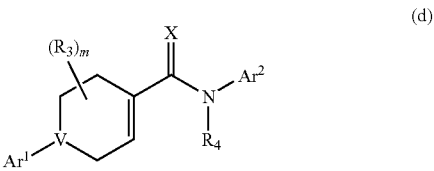

(d)

wherein V is N or CH, $R_3$ is $C_{1-10}$ alkyl, halo, and the like, m is 0 or 1, $Ar^1$ is pyridinyl, pyrimidinyl, pyrazinyl, pyridazinyl, or thiadiazolyl, X is O or S, $Ar^2$ is phenyl, pyridinyl, cyclohexyl, cyclohexenyl, and the like and are reported as vanilloid receptor inhibitors.

However, none of these compounds has the structural characteristics of the compounds of the present invention wherein the compounds of the invention contain a chiral carbon center in the tetrahydropyridine ring and possess unexpected efficacy as TRPV1 antagonists.

SUMMARY

One aspect of the invention is directed towards compounds of formula (I), or pharmaceutical salts, prodrugs, salts of prodrugs, or combinations thereof,

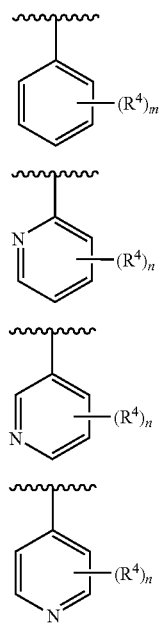

(I)

wherein
$R^1$ represents formula (i), (ii), (iii), or (iv)

(i)

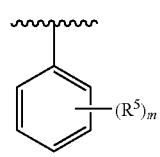

(ii)

(iii)

(iv)

$R^2$ represents formula (v), (vi), (vii), (viii), (ix), (x), (xi), or (xii)

(v)

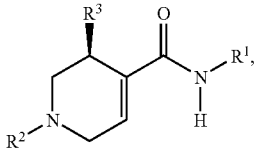

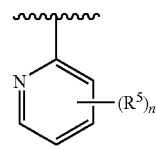

(vi)

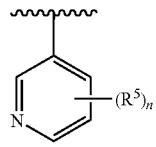

(vii)

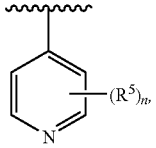

(viii)

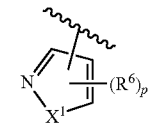

(ix)

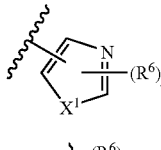

(x)

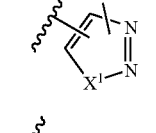

(xi)

(xii)

$R^3$ is $C_{1-6}$ alkyl;
$R^4$ represents optional substituents of $R^1$, and is, at each occurrence, independently alkyl, alkenyl, alkynyl, —CN, halogen, —$OR^a$, —$NO_2$, —$N(R^a)(R^b)$, —$N(R^b)C(O)R^a$, —$N(R^b)S(O)_2R^a$, —$N(R^b)C(O)OR^a$, —$N(R^b)C(O)N(R^a)(R^b)$, —$N(R^b)S(O)_2N(R^a)(R^b)$, —$C(O)R^a$, —$C(O)OR^a$, —$C(O)N(R^a)(R^b)$, —$S(O)_2R^a$, —$S(O)_2OR^a$, —$S(O)_2N(R^a)$ $(R^b)$, —$(CR^dR^e)_q$—CN, haloalkyl, —$(CR^dR^e)_q$—$OR^a$, —$(CR^dR^e)_q$—$NO_2$, —$(CR^dR^e)_q$—$N(R^a)(R^b)$, —$(CR^dR^e)_q$—$N(R^b)C(O)R^a$, —$(CR^dR^e)_q$—$N(R^b)S(O)_2R^a$, —$(CR^dR^e)_q$—$N(R^b)C(O)OR^a$, —$(CR^dR^e)_q$—$N(R^b)C(O)N$ $(R^a)(R^b)$, —$(CR^dR^e)_q$—$N(R^b)S(O)_2N(R^a)(R^b)$, —$(CR^dR^e)_q$—$C(O)R^a$, —$(CR^dR^e)_q$—$C(O)OR^a$, —$(CR^dR^e)_q$—$C(O)N(R^a)(R^b)$, —$(CR^dR^e)_q$—$S(O)_2R^a$, —$(CR^dR^e)_q$—$S(O)_2OR^a$, or —$(CR^dR^e)_q$—$S(O)_2N(R^a)(R^b)$;

$R^5$ and $R^6$ are optional substituents of $R^2$, and each of which at each occurrence is independently alkyl, alkenyl, alkynyl, halogen, —CN, halogen, —$OR^a$, —$NO_2$, —$N(R^a)$ $(R^b)$, or haloalkyl;

$R^a$ and $R^b$, at each occurrence, are each independently hydrogen, alkyl, or haloalkyl;

$R^d$ and $R^e$, at each occurrence, are each independently hydrogen, alkyl, halogen, or haloalkyl;

$X^1$ is O or S;
m is 0, 1, 2, 3, 4, or 5;
n is 0, 1, 2, 3, or 4;

p is 0, 1, or 2;
q is 1, 2, 3, or 4; and
s is 0 or 1.

Another aspect of the present invention is a pharmaceutical composition comprising a compound of formula (I), or a pharmaceutically acceptable salt thereof, and one or more pharmaceutically acceptable carriers, alone or in combination with acetaminophen, with one or more nonsteroidal anti-inflammatory drugs (NSAID), or a combination thereof.

Another aspect of the present invention is a method of treating acute cerebral ischemia, chronic pain, neuropathic pain, inflammatory pain, post herpetic neuralgia, neuropathies, neuralgia, diabetic neuropathy, HIV-related neuropathy, nerve injury, rheumatoid arthritic pain, osteoarthritic pain, burns, back pain, visceral pain, cancer pain, dental pain, headache, migraine, carpal tunnel syndrome, fibromyalgia, neuritis, sciatica, pelvic hypersensitivity, pelvic pain, menstrual pain; bladder disease such as incontinence, micturition disorder, renal colic and cystitis; inflammation such as burns, rheumatoid arthritis and osteoarthritis; neurodegenerative disease such as stroke, post stroke pain and multiple sclerosis; pulmonary disease such as asthma, cough, chronic obstructive pulmonary disease (COPD) and broncho constriction; gastrointestinal disease such as gastroesophageal reflux disease (GERD), dysphagia, ulcer, irritable bowel syndrome (IBS), inflammatory bowel disease (IBD), colitis and Crohn's disease; ischemia such as cerebrovascular ischemia; emesis such as cancer chemotherapy-induced emesis, or obesity, said method comprising the step of administering a therapeutically effective amount of a compound of formula (I), or a pharmaceutically acceptable salt thereof, to a subject in need thereof, alone or in combination with acetaminophen, one or more nonsteroidal anti-inflammatory drug (NSAID), or a combination thereof, and with or without one or more pharmaceutically acceptable carrier.

Further, the present invention provides the use of compounds of the present invention or a pharmaceutically acceptable salt thereof, in the manufacture of a medicament for the treatment of the disease conditions described above, with or without one or more pharmaceutically acceptable carrier, and alone, or in combination with acetaminophen, one or more nonsteroidal anti-inflammatory drug (NSAID), or a combination thereof.

These and other objects of the invention are described in the following paragraphs. These objects should not be deemed to narrow the scope of the invention.

DETAILED DESCRIPTION

Compounds of formula (I) are disclosed in this invention

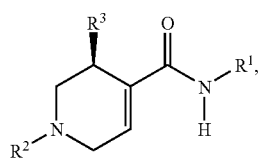

(I)

wherein $R^1$, $R^2$, and $R^3$ are as defined above in the Summary of the Invention and below in the Detailed Description. Compositions comprising such compounds and methods for treating conditions and disorders using such compounds and compositions are also disclosed.

For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds, which can be isolated from a reaction mixture.

a). DEFINITIONS

As used in the specification and the appended claims, unless specified to the contrary, the following terms have the meaning indicated:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkyl" as used herein, means a saturated, straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 3-methylhexyl, 2,2-dimethylpentyl, 2,3-dimethylpentyl, n-heptyl, n-octyl, n-nonyl, and n-decyl. The term "$C_{1-6}$ alkyl" as used herein, means an alkyl group, as defined herein, containing 1, 2, 3, 4, 5, or 6 carbon atom in the chain.

The term "halo" or "halogen" as used herein, means —Cl, —Br, —I or —F.

The term "haloalkyl" as used herein, means an alkyl group, as defined herein, in which one, two, three, four, five, six, or seven hydrogen atoms are replaced by halogen. The term "lower haloalkyl" means a $C_{1-6}$ alkyl group, as defined herein, in which one, two, three, four, five, six, or seven hydrogen atoms are replaced by halogen. Representative examples of haloalkyl and lower haloalkyl include, but are not limited to, chloromethyl, 2-fluoroethyl, 2,2-difluoroethyl, trifluoromethyl, 2,2,2-trifluoroethyl, difluoromethyl, pentafluoroethyl, 2-chloro-3-fluoropentyl, and 2-iodoethyl.

b) COMPOUNDS OF THE INVENTION

Compounds of the invention have the formula (I) as described above.

Particular values of variable groups in compounds of formula (I) are as follows. Such values may be used where appropriate with any of the other values, definitions, claims or embodiments defined hereinbefore or hereinafter.

In compounds of formula (I), $R^1$ represents formula (i), (ii), (iii), or (iv)

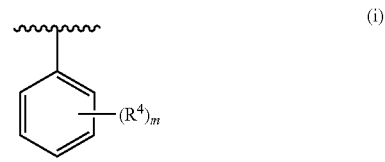

(i)

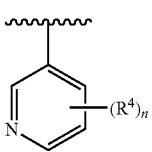

(ii)

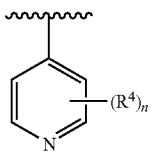

(iii)

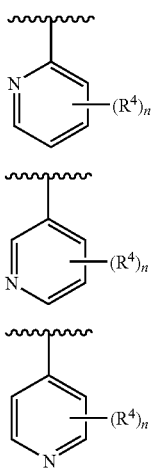

(iv)

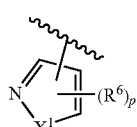

(ix)

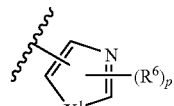

(x)

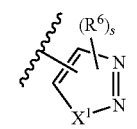

(xi)

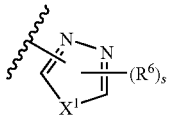

(xii)

wherein $R^4$, m, and n are as defined in the Summary. In one embodiment, $R^1$ represents formula (i). In another embodiment, $R^1$ represents formula (ii), (iii), or (iv). In yet another embodiment, $R^1$ represents formula (iii). $R^4$, for example, is $C_{1-6}$ alkyl (for example, tert-butyl), halogen, —$(CR^dR^e)_q$—CN, lower haloalkyl, or —$S(O)_2R^a$ wherein $R^a$, $R^d$, $R^e$, and q are as disclosed in the Summary. $R^a$, for example, is haloalkyl. $R^d$ and $R^e$ are the same or different and are, for example, hydrogen or $C_{1-6}$ alkyl. A further example of $R^d$ and $R^e$ is methyl. q, for example, is 1 or 2. A further example of q is 1. $R^a$, for example, is $C_{1-6}$ alkyl or lower haloalkyl. A further example of $R^a$ is lower haloalkyl. A yet further example of $R^a$ is trifluoromethyl. Compounds of the invention include those wherein $R^4$ is located at the fourth position of the ring as represented by $R^1$, relative to the point of connection of the ring to the N(H) moiety of formula (I).

$R^2$ represents formula (v), (vi), (vii), (viii), (ix), (x), (xi), or (xii)

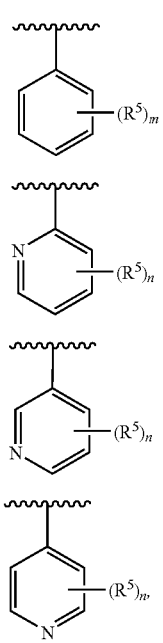

(v)

(vi)

(vii)

(viii)

wherein $X^1$, $R^6$, m, n, p, and s are as defined in the Summary. In one embodiment, $R^2$ represents formula (v). In another embodiment, $R^2$ represents formula (vi). In yet another embodiment, $R^2$ represents formula (vii) or (viii). In a further embodiment, $R^2$ represents formula (ix), (x), (xi), or (xii). $R^5$, for example, is $C_{1-6}$ alkyl (such as, but not limited to, methyl), halogen, or haloalkyl such as, but not limited to, trifluoromethyl. m and n are the same or different and are, for example, 1 or 2. A further example of m and n is 1. Examples of the compounds of invention include those wherein $R^5$ is located at the 2-position of the ring as represented by $R^2$, relative to the point of connection of $R^2$ to the nitrogen atom of formula (I).

$R^3$ is $C_{1-6}$ alkyl. In one embodiment, $R^3$ is methyl.

It is appreciated that the present invention contemplates compounds of formula (I) with combinations of the above embodiments, including particular, more particular and preferred embodiments.

Accordingly, one aspect of the invention relates to a group of compounds of formula (I), or pharmaceutically acceptable salts thereof, wherein $R^3$ is methyl, $R^1$ is formula (i), and $R^2$, $R^4$, and n are as disclosed in the Summary.

Another aspect of the invention relates to a group of compounds of formula (I), or pharmaceutically acceptable salts thereof, wherein $R^3$ is methyl, $R^1$ is formula (ii), (iii), or (iv), and $R^2$, $R^4$, and n are as disclosed in the Summary.

Yet another aspect of the invention relates to a group of compounds of formula (I), or pharmaceutically acceptable salts thereof, wherein $R^3$ is methyl, $R^1$ is formula (iii), and $R^2$, $R^4$, and n are as disclosed in the Summary.

For all the foregoing groups of compounds of formula (I), examples of a subgroup include those wherein $R^2$ is formula (v), and $R^5$ and m are as defined in the Summary.

Other examples of a subgroup include those wherein $R^2$ is formula (vi), and $R^5$ and n are as defined in the Summary.

Yet other examples of a subgroup include those wherein $R^2$ is formula (vii) or (viii), and $R^5$ and n are as defined in the Summary.

Yet other examples of a subgroup include those wherein $R^2$ is formula (ix), (x), (xi), or (xii), and $X^1$, $R^6$, p, and s are as defined in the Summary.

For the above groups and subgroups of compounds of formula (I), examples of $R^4$ include, but are not limited to, $C_{1-6}$ alkyl (for example, tert-butyl), halogen, $—(CR^dR^e)_q—$ CN, lower haloalkyl, or $—S(O)_2R^a$ wherein $R^a$, $R^d$, $R^e$, and $q$ are as disclosed in the Summary. $R^a$, for example, is haloalkyl. $R^d$ and $R^e$ are the same or different and are, for example, hydrogen or $C_{1-6}$ alkyl. A further example of $R^d$ and $R^e$ is methyl. q, for example, is 1 or 2. A further example of q is 1. $R^a$, for example, is $C_{1-6}$ alkyl or lower haloalkyl. A further example of $R^a$ is lower haloalkyl. A yet further example of $R^a$ is trifluoromethyl. Examples of $R^5$ include, but are not limited to, $C_{1-6}$ alkyl (such as, but not limited to, methyl), halogen, or haloalkyl such as, but not limited to, trifluoromethyl. m and n are the same or different and are, for example, 1 or 2. A further example of m and n is 1.

A preferred embodiment of the invention relates to compounds of formula (II), or pharmaceutically acceptable salts thereof,

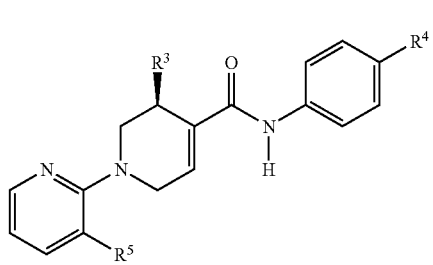

(II)

wherein $R^3$, $R^4$, and $R^5$ have the values as disclosed in the Summary and the Detailed Description sections.

Compounds of the present invention contain an asymmetrically substituted carbon atom in the tetrahydropyridine ring of formula (I) and (II) wherein the configuration of the carbon atom bearing $R^3$ is assigned as (3S) isomer as defined by the IUPAC 1974 Recommendations for Section E, Fundamental Stereochemistry, Pure Appl. Chem. 1976 45, 13-30. It is understood that compounds of the invention are essentially free of the corresponding (3R) isomer as depicted in formula (III). By "essentially free" is meant greater than about 90% free of the (3R) enantiomers of the compounds, for example, greater than about 95% free of the (3R) enantiomers of the compounds, or greater than about 98% free of the (3R) enantiomers of the compounds.

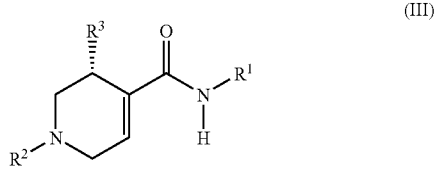

(III)

It will be appreciated two or more asymmetric centers may be present in the compounds of the invention, hence several diastereomers and enantiomers of the exemplified structures will often be possible, and that pure diastereomers and enantiomers represent preferred embodiments. It is intended that pure diasteromers, pure enantiomers, and mixtures thereof, are within the scope of the invention.

The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or heterocycle are designated as being of cis or trans configuration.

Within the present invention it is to be understood that compounds disclosed herein may exhibit the phenomenon of tautomerism and all tautomeric isomers are included in the scope of the invention.

c) GENERAL SYNTHESIS

This invention is intended to encompass compounds of the invention when prepared by synthetic processes or by metabolic processes. Preparation of the compounds of the invention by metabolic processes include those occurring in the human or animal body (in vivo) or processes occurring in vitro.

The synthesis of compounds of formula (I) wherein the groups $R^1$, $R^2$, and $R^3$ have the meanings as set forth in the summary section unless otherwise noted, is exemplified in the accompanying Schemes 1 and 2.

As used in the descriptions of the schemes and the examples, certain abbreviations are intended to have the following meanings: dba for dibenzylideneacetone; THF for tetrahydrofuran; Tf or triflate for trifluoromethanesulfonate, BOC for tert-butoxycarbonyl; and HPLC for high performance liquid chromatography.

The compounds of formula (I) can be produced by, for example, the following reaction scheme:

Scheme 1

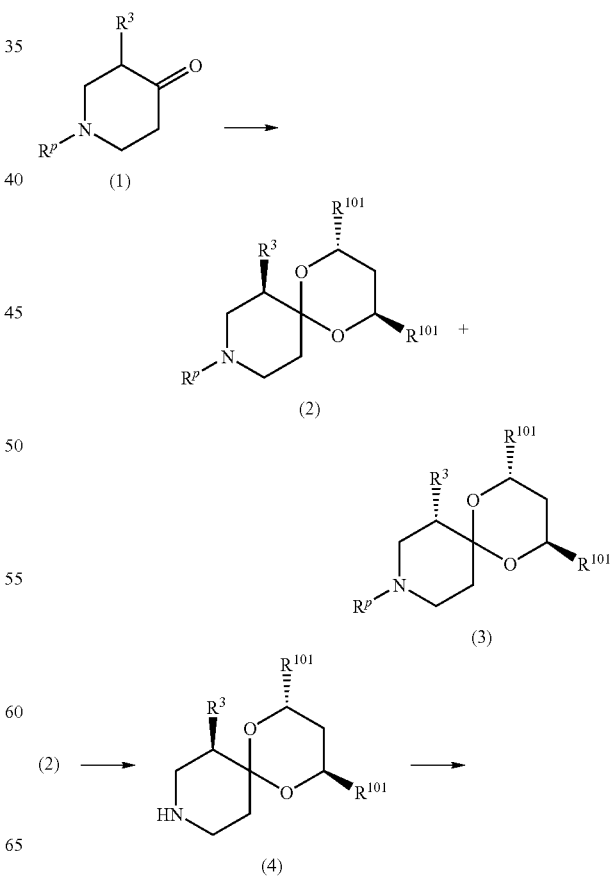

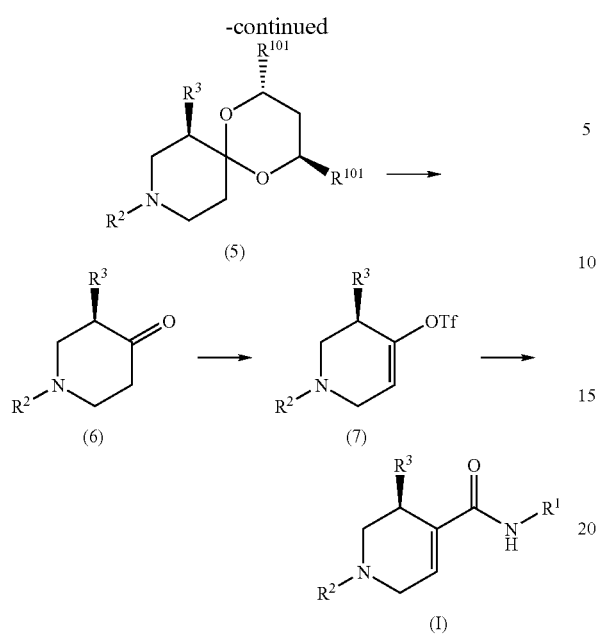

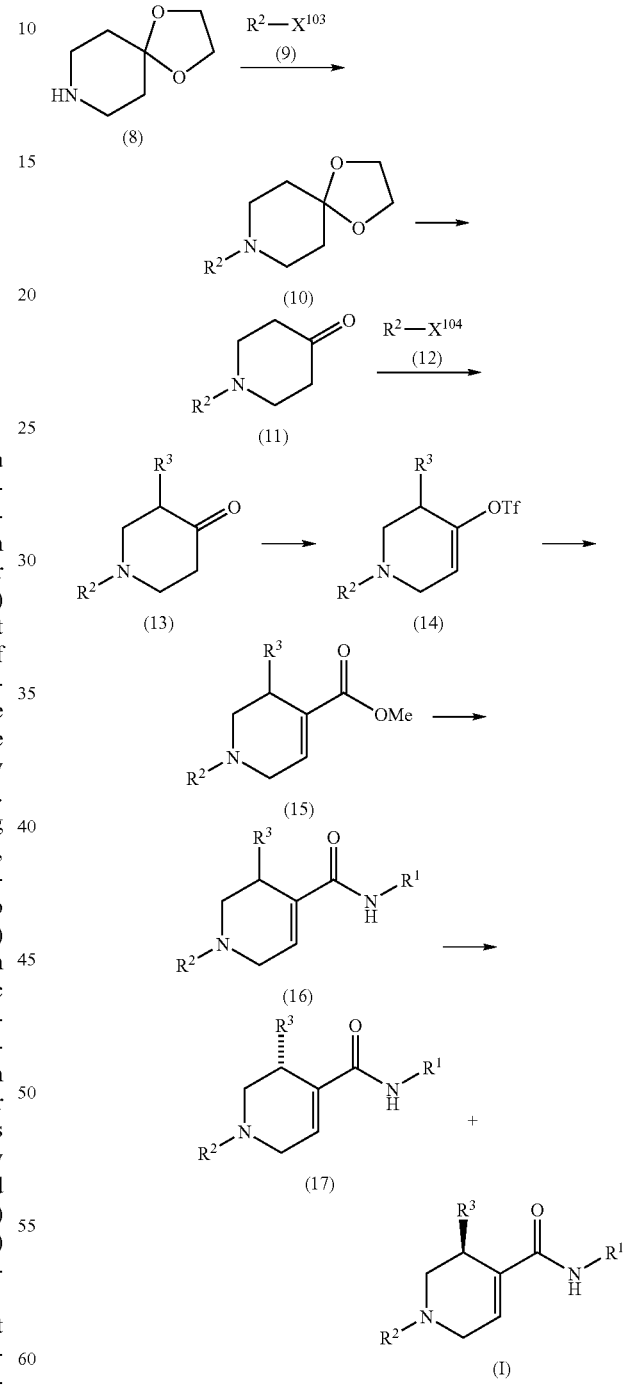

(R)-enantiomers of general formula (I) can be prepared from compounds of formula (3) using similar procedures as outlined above in Scheme 1.

The compounds of formula (I) can also be produced by, for example, using the following reaction scheme:

For example, piperidone compounds of general formula (1) wherein $R^p$ is a nitrogen protecting group, can be subjected to reaction with chiral diol, such as, (2R,4R)-pentane-2,4-diol or its enantiomer in the presence of excess acid such as p-toluenesulfonic acid and in a solvent such as benzene or toluene to provide a mixture of diastereomers, (2) and (3) wherein $R^{101}$ is alkyl. The reaction is generally conducted at the reflux temperature of the solvent employed. Examples of the nitrogen protecting groups are known in the art. Non-limiting examples of the nitrogen protecting groups include benzyl, tert-butoxycarbonyl, and benzyloxycarbonyl. The diasteromers can be separated by silica gel chromatography to afford diastereomerically pure ketals of formula (2) or (3). The nitrogen protecting group of (2) can be removed using methodologies known by one skilled in the art, for example, by hydrogenolysis in the presence of a catalyst such as palladium hydroxide or by treatment with trifluoroacetic acid, to provide the free amine of formula (4). (4) is converted to (5) by treatment with compounds of formula $R^2X^{102}$ wherein $X^{102}$ is a leaving group such as triflate, halogen or aromatic sulfonates (for example, benzenesulfonate or p-toluenesulfonate) in the presence of a base such as potassium carbonate. The reaction is generally performed in a solvent such as dimethylsulfoxide, and at elevated temperature, for example, at about 70 to about 150° C. Conversion of the ketals (5) to the corresponding ketones (6) can be accomplished by treatment with an acid such as, but not limited to, acetic acid in water, at ambient temperature (about 20 to about 25° C.) until the reaction is complete. Treatment of the ketones (6) with a triflating agent such as, but not limited to, 1,1,1-trifluoro-N-phenyl-N-(trifluoromethylsulfonyl)methanesulfonamide, in the presence of an amide base such as, but not limited to, lithium diisopropylamide or lithium bis(trimethylsilyl)amide, provides enol triflates of formula (7). Thereafter (7) can be transformed to compounds of general formula (I) using, for example, carbon monoxide, and amines of formula $R^1NH_2$, in the presence of a palladium catalyst (for example, palladium (II) acetate) and a ligand (for example, triphenylphosphine or 2-dicyclohexylphosphine-2'-(N,N-dimethylamino)biphenyl), and a base such as triethylamine.

For example, a protected piperidone such as 1,4-dioxa-8-azaspiro[4.5]decane (8) can be reacted with electrophiles of general formula (9), wherein $X^{103}$ is a leaving group such as halogen or triflate to provide products of the general formula (10). The reaction is generally performed in the presence of a base such as potassium carbonate, in a solvent such as dimethylsulfoxide, and at elevated temperature, for example, at about 70 to about 150° C. Alternatively, such transformation can be effected by a palladium catalyst, in the presence of a ligand, and a base, at an elevated temperature (for example, about 80 to about 150° C.), and in a solvent such as an aromatic hydrocarbon (for example, toluene). An example of suitable palladium catalyst is tris(dibenzylideneacetone)dipalladium(0). Non-limiting examples of suitable bases are cesium fluoride, potassium fluoride, and sodium tert-butoxide. An example of a suitable ligand is 2,2'-bis(diphenylphosphino)-1,1'binaphthyl. Conversion of the ketals (10) to the corresponding ketones (11) can be accomplished by treatment with an acid such as, but not limited to, hydrochloric acid at ambient temperature (about 20 to about 25° C.) until the reaction is complete. Treatment of the ketones (11) with an alkylating agent $R^3X^{104}$ (12) wherein $X^{104}$ is a leaving group such as halogen, triflate, or sulfate, in the presence of base and a solvent provides alkylated products of formula (13). Examples of suitable bases for the transformation include, but are not limited to sodium hydride and an amide base (for example, lithium diisopropylamide or lithium bis(trimethylsilyl)amide). Treatment of the ketones (13) with a triflating agent such as, but not limited to, 1,1,1-trifluoro-N-phenyl-N-(trifluoromethylsulfonyl)methanesulfonamide, in the presence of an amide base such as, but not limited to, lithium diisopropylamide or lithium bis(trimethylsilyl) amide, provides enol triflates of formula (14). Thereafter (14) can be transformed to methyl esters of general formula (15) using, for example, carbon monoxide and methanol, in the presence of a palladium catalyst (for example, palladium (II) acetate) and a ligand (for example, triphenylphosphine or 2-dicyclohexylphosphine-2'-(N,N-dimethylamino)biphenyl), and a base such as triethylamine. The esters (15) can be transformed to compounds of general formula (16) using trimethylaluminum and amines of formula $R^1NH_2$ in a solvent such toluene or dichloromethane. Single enantiomers (17) and (I) can be separated by chiral HPLC using a chiral column such as, but not limited to, a Chiralcel OD or Chiralcel AS column (Chiral Technologies Inc., West Chester, Pa.) and solvent mixtures containing methanol, hexane, and dichloromethane.

It will be appreciated that the synthetic schemes and specific examples as illustrated in the synthetic examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Synthetic Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis (3$^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

d) EXAMPLES

Example 1

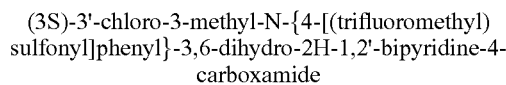
(3S)-3'-chloro-3-methyl-N-{4-[(trifluoromethyl)sulfonyl]phenyl}-3,6-dihydro-2H-1,2'-bipyridine-4-carboxamide Example 1A

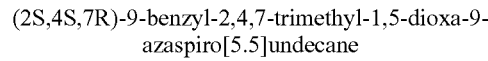
(2S,4S,7R)-9-benzyl-2,4,7-trimethyl-1,5-dioxa-9-azaspiro[5.5]undecane To a solution of 1-benzyl-3-methylpiperidin-4-one (Acros, 62.09 g, 305.4 mmol) and (2S,4S)-pentane-2,4-diol (TCI-US, 34.06 g, 327.0 mmol) in benzene (800 mL) was added p-toluenesulfonic acid mono hydrate (69.72 g, 404.9 mmol). The flask was fitted with a Dean-Stark trap and heated to reflux. The reaction mixture was cooled after 16 hours of reflux, concentrated to a total volume of about 500 mL and transferred to an Erlenmeyer flask with ethyl acetate. A sodium bicarbonate solution (500 mL) added with stirring and the mixture was further neutralized with solid $Na_2CO_3$ (35 g). The layers were partitioned, the organic phase washed with sodium bicarbonate, dried ($Na_2SO_4$) and concentrated to yield approximately 95 g of crude material. The residue was purified in 15 g batches by silica gel chromatography (Analogix SF-65-600 g; 35 micron silica; elution with 10% ethyl acetate-hexane) at 50 mL/min to provide 42.33 g of the first eluting isomer, (2S,4S,7R)-9-benzyl-2,4,7-trimethyl-1,5-dioxa-9-azaspiro[5.5]undecane. $^1$H NMR (300 MHz, DMSO-d$_6$) δ 7.33-7.19 (m, 5H), 4.07-3.86 (m, 2H), 3.40 (ABq, 2H, $J_{AB}$=13.5 Hz, δν$_{AB}$=23.3 Hz), 2.41-2.20 (m, 4H), 1.90-1.76 (m, 2H), 1.59-1.47 (m, 3H), 1.12 (d, 3H, J=6.4 Hz), 1.11 (d, 3H, J=6.4 Hz), 0.90 (d, 3H, J=7.1 Hz); MS (DCI/NH$_3$) m/e 290 (M+H)$^+$.

Example 1B (2S,4S,7S)-9-benzyl-2,4,7-trimethyl-1,5-dioxa-9-azaspiro[5.5]undecane The title compound was the later eluting isomer obtained from the purification of the reaction mixture in Example 1A (40.82 g). $^1$H NMR (300 MHz, DMSO-d$_6$) δ 7.35-7.19 (m, 5H), 4.04-3.91 (m, 2H), 3.40 (ABq, 2H, J$_{AB}$=13.5 Hz, δν$_{AB}$=17.1 Hz), 2.44-2.38 (m, 2H), 2.26-2.15 (m, 1H), 2.11-2.04 (m, 1H), 2.00-1.93 (m, 1H), 1.82-1.71 (m, 1H), 1.61-1.42 (m, 3H), 1.13 (d, 3H, J=6.0 Hz), 1.11 (d, 3H, J=6.3 Hz), 0.87 (d, 3H, J=6.8 Hz); MS (DCI/NH$_3$) m/e 290 (M+H)$^+$.

Example 1C (2S,4S,7R)-2,4,7-trimethyl-1,5-dioxa-9-azaspiro[5.5]undecane

To a solution of (2S,4S,7R)-9-benzyl-2,4,7-trimethyl-1,5-dioxa-9-azaspiro[5.5]undecane from Example 1A (20.30 g, 70.20 mmol) in methanol (300 mL) was added palladium hydroxide (0.986 g, 7.02 mmol) and the mixture stirred under 60 psi pressure of hydrogen. After 4 hours, the mixture was filtered and concentrated to provide 13.71 g (98%) of the title compound as an oil. $^1$H NMR (300 MHz, CDCl$_3$) δ 4.06-3.97 (m, 2H), 2.94 (dd, 1H, J=12.7, 4.0 Hz), 2.87 (dd, 2H, J=5.2, 5.2 Hz), 2.66 (dd, 1H, J=12.7, 5.6 Hz), 1.92-1.85 (m, 1H), 1.82-1.73 (m, 1H), 1.63-1.53 (m, 4H), 1.20 (d, 3H, J=6.4 Hz), 1.19 (d, 3H, J=6.4 Hz), 0.96 (d, 3H, J=7.1 Hz); MS (DCI/NH$_3$) m/e 200 (M+H)$^+$.

Example 1D (2S,4S,7R)-9-(3-chloropyridin-2-yl)-2,4,7-trimethyl-1,5-dioxa-9-azaspiro[5.5]undecane To a solution of the product from Example 1C (13.71 g, 68.79 mmol) in dimethylsulfoxide (70 mL) was added potassium carbonate (19.02 g, 137.6 mmol) and 2,3-dichloropyridine (12.22 g, 82.57 mmol). The reaction mixture was heated at 90° C. and stirred for 96 hours. The reaction mixture was poured into ethyl acetate (200 mL), washed with saturated sodium bicarbonate, dried (Na$_2$SO$_4$) and concentrated. The residue was purified by silica gel chromatography (elution with 25% ethyl acetate-hexane) to provide 17.91 g (84%) of the title compound. $^1$H NMR (300 MHz, CDCl$_3$) δ 8.14 (dd, 1H, J=4.7, 1.7 Hz), 7.54 (dd, 1H, J=7.8, 1.7 Hz), 6.77 (dd, 1H, J=7.8, 4.8 Hz), 4.13-3.97 (m, 2H), 3.47-3.28 (m, 4H), 2.17-2.00 (m, 2H), 1.85-1.77 (m, 1H), 1.69-1.54 (m, 2H), 1.21 (d, 6H, J=6.4 Hz), 1.08 (d, 3H, J=7.1 Hz); MS (DCI/NH$_3$) m/e 311 (M+H)$^+$.

Example 1E (3R)-1-(3-chloropyridin-2-yl)-3-methylpiperidin-4-one

A solution of the product from Example 1D (9.08 g, 29.2 mmol) in acetic acid (50.0 mL) and water (50 mL) was stirred at room temperature for 2 hours. The reaction mixture was made basic with saturated sodium bicarbonate, the layers partitioned and the aqueous layer back extracted with ethyl acetate (2×100 mL). The organic phases were combined, dried (Na$_2$SO$_4$), and concentrated. The residue was purified by silica gel chromatography (elution with 25% ethyl acetate-hexane) to provide 6.00 g (91%) of the title compound. $^1$H NMR (300 MHz, CDCl$_3$) δ 8.19 (dd, 1H, J=4.8, 1.6 Hz), 7.63 (dd, 1H, J=7.9, 1.6 Hz), 6.88 (dd, 1H, J=7.5, 4.8 Hz), 4.16-4.05 (m, 2H), 3.33-3.23 (m, 1H), 2.96 (dd, 1H, J=12.3, 10.7 Hz), 2.86-2.73 (m, 2H), 2.50 (ddd, 1H, J=14.3, 3.2, 3.2 Hz), 1.09 (d, 3H, J=6.8 Hz); MS (DCI/NH$_3$) m/e 225 (M+H)$^+$.

Example 1F (R)-1-(3-chloropyridin-2-yl)-3-methyl-1,2,3,6-tetrahydropyridin-4-yl trifluoromethanesulfonate To a solution of the product from Example 1E (6.00 g, 26.7 mmol) and 1,1,1-trifluoro-N-phenyl-N-(trifluoromethylsulfonyl)methanesulfonamide (10.5 g, 29.4 mmol) in tetrahydrofuran (100 mL) at −78° C. was added lithium bis(trimethylsilyl)amide (1.0 M in tetrahydrofuran, 32.0 mL) and the reaction mixture was stirred for 1 hour. The reaction mixture was warmed to room temperature and stirred for an additional 1 hour, concentrated, and taken up in ethyl acetate (200 mL). The organic phase was washed with saturated sodium bicarbonate, brine, dried (Na$_2$SO$_4$), and concentrated. The residue was purified by silica gel chromatography (elution with 25% ethyl acetate-hexane) to provide 8.00 g (84%) of the title compound. $^1$H NMR (300 MHz, CDCl$_3$) δ 8.16 (dd, 1H, J=4.8, 1.7 Hz), 7.60 (dd, 1H, J=7.8, 1.7 Hz), 6.86 (dd, 1H, J=7.8, 4.8 Hz), 5.88-5.86 (m, 1H), 4.04-4.01 (m, 2H), 3.78 (ddd, 1H, J=12.9, 4.8, 0.7 Hz), 3.17 (dd, 1H, J=12.5, 6.8 Hz), 2.96-2.89 (m, 1H), 1.25 (d, 3H, J=7.1 Hz); MS (DCI/NH$_3$) m/e 357 (M+H)$^+$.

Example 1G (3S)-3'-chloro-3-methyl-N-{4-[(trifluoromethyl)sulfonyl]phenyl}-3,6-dihydro-2H-1,2'-bipyridine-4-carboxamide A solution of palladium (II) acetate (0.883 g, 3.94 mmol), the product from Example 1F (7.0 g, 19.68 mmol), triethylamine (5.48 mL, 39.4 mmol), 2-dicyclohexylphosphine-2'-(N,N-dimethylamino)biphenyl (3.10 g, 7.87 mmol) and 4-(trifluoromethylsulfonyl)aniline (5.76 g, 25.6 mmol) in N,N-dimethylformamide (20 mL) was placed under 1 atmosphere of carbon monoxide and stirred at room temperature for 2 hours. The reaction mixture was concentrated to approximately 10 mL, poured into 1.5 L of ethyl acetate, washed with saturated sodium bicarbonate, dried (Na$_2$SO$_4$), and concentrated. The residue was purified by silica gel chromatography (gradient elution from 0% to 20% ethyl acetate-[50% CH$_2$Cl$_2$-hexane] to provide the title compound as a white solid. $^1$H NMR (300 MHz, CDCl$_3$) δ 8.20 (d, 1H, J=4.8, 1.7 Hz), 8.02 (d, 2H, J=8.8 Hz), 7.90 (d, 2H, J=9.1 Hz), 7.81 (br s, 1H), 7.63 (dd, 1H, J=7.8, 1.7 Hz), 6.88 (dd, 1H, J=7.5, 4.8 Hz), 6.65 (dd, 1H, J=3.1, 3.1 Hz), 4.20-3.97 (m, 2H), 3.64 (dd, 1H, J=12.9, 4.1 Hz), 3.34 (dd, 1H, J=12.9, 4.4 Hz), 3.11-3.07 (m, 1H), 1.29 (d, 3H, J=6.4 Hz); MS (DCI/NH$_3$) m/e 460 (M+H)$^+$; [α]$^{23}_D$ +34.0° (c 1.0, CH$_3$OH).

Example 2

(3S)-3'-chloro-3-methyl-N-[4-(trifluoromethyl)phenyl]-3,6-dihydro-2H-1,2'-bipyridine-4-carboxamide

Example 2A (2R,4R,7S)-9-benzyl-2,4,7-trimethyl-1,5-dioxa-9-azaspiro[5.5]undecane The title compound (6.27 g) was obtained as the first eluting isomer when prepared using similar procedure as described in Example 1A, substituting toluene for benzene and substituting (2R,4R)-pentane-2,4-diol for (2S,4S)-pentane-2,4-diol. $^1$H NMR (300 MHz, DMSO-d$_6$) δ 7.33-7.19 (m, 5H), 4.07-3.86 (m, 2H), 3.40 (ABq, 2H, J$_{AB}$=13.5 Hz, δv$_{AB}$=23.3 Hz), 2.41-2.20 (m, 4H), 1.90-1.76 (m, 2H), 1.59-1.47 (m, 3H), 1.12 (d, 3H, J=6.4 Hz), 1.11 (d, 3H, J=6.4 Hz), 0.90 (d, 3H, J=7.1 Hz); MS (DCI/NH$_3$) m/e 290 (M+H)$^+$.

Example 2B (2R,4R,7R)-9-benzyl-2,4,7-trimethyl-1,5-dioxa-9-azaspiro[5.5]undecane The title compound (5.87 g) was the later eluting isomer obtained from the purification of the reaction mixture from Example 2A. $^1$H NMR (300 MHz, DMSO-d$_6$) δ 7.35-7.19 (m, 5H), 4.04-3.91 (m, 2H), 3.40 (ABq, 2H, J$_{AB}$=13.5 Hz, δv$_{AB}$=17.1 Hz), 2.44-2.38 (m, 2H), 2.26-2.15 (m, 1H), 2.11-2.04 (m, 1H), 2.00-1.93 (m, 1H), 1.82-1.71 (m, 1H), 1.61-1.42 (m, 3H), 1.13 (d, 3H, J=6.0 Hz), 1.11 (d, 3H, J=6.3 Hz), 0.87 (d, 3H, J=6.8 Hz); MS (DCI/NH$_3$) m/e 290 (M+H)$^+$.

Example 2C (2R,4R,7R)-2,4,7-trimethyl-1,5-dioxa-9-azaspiro[5.5]undecane

To a solution of (2R,4R,7R)-9-benzyl-2,4,7-trimethyl-1,5-dioxa-9-azaspiro[5.5]undecane (880 mg, 3.04 mmol) from Example 2B in methanol (25 mL) was added palladium hydroxide (82 mg) and the mixture stirred under 1 atmosphere pressure of hydrogen. After 5 h, the mixture was filtered and concentrated to provide 567 mg (94%) of the title compound as an oil. $^1$H NMR (300 MHz, CDCl$_3$) δ 4.11-3.97 (m, 2H), 2.93-2.71 (m, 3H), 2.61 (dd, 1H, J=12.3, 8.7 Hz), 1.97 (ddd, 1H, J=13.9, 5.6, 3.6 Hz), 1.79-1.70 (m, 1H), 1.65-1.47 (m, 4H), 1.21 (d, 3H, J=6.4 Hz), 1.19 (d, 3H, J=6.4 Hz), 0.95 (d, 3H, J=6.7 Hz); MS (DCI/NH$_3$) m/e 200 (M+H)$^+$.

Example 2D (2R,4R,7R)-9-(3-chloropyridin-2-yl)-2,4,7-trimethyl-1,5-dioxa-9-azaspiro[5.5]undecane To a solution of the product from Example 2C (1.00 g; 5.02 mmol) in dimethylsulfoxide (20 mL) was added potassium carbonate (693 mg, 5.02 mmol) and 2,3-dichloropyridine (891 mg, 6.02 mmol). The reaction mixture was heated at 90° C. and stirred for 96 hours. The reaction mixture was poured into ethyl acetate (200 mL), washed with saturated sodium bicarbonate, dried (Na$_2$SO$_4$) and concentrated. The residue was purified by silica gel chromatography (elution with 25% ethyl acetate-hexane) to provide 1.33 g (85%) of the title compound. $^1$H NMR (300 MHz, CDCl$_3$) δ 8.15 (dd, 1H, J=4.8, 1.7 Hz), 7.56 (dd, 1H, J=7.8, 1.4 Hz), 6.78 (dd, 1H, J=7.5, 4.8 Hz), 4.14-4.02 (m, 2H), 3.53-3.44 (m, 2H), 3.27-3.19 (m, 1H), 3.11 (dd, 1H, J=12.2, 8.5 Hz), 2.18-2.00 (m, 2H), 1.83 (ddd, 1H, J=13.2, 9.5 Hz), 1.70-1.50 (m, 2H), 1.22 (d, 3H, J=6.4 Hz), 1.21 (d, 3H, J=6.4 Hz), 1.05 (d, 3H, J=6.8 Hz); MS (DCI/NH$_3$) m/e 311 (M+H)$^+$.

Example 2E (3R)-1-(3-chloropyridin-2-yl)-3-methylpiperidin-4-one

A solution of the product from Example 2D (1.31 g, 4.21 mmol) in acetic acid (10.0 mL) and water (30.0 mL) was stirred at room temperature for 2 hours. The reaction mixture was made basic with saturated sodium bicarbonate, the layers partitioned and the aqueous layer back extracted with ethyl acetate (2×100 mL). The organic phases were combined, dried (Na$_2$SO$_4$), and concentrated. The residue was purified by silica gel chromatography (elution with 25% ethyl acetate-hexane) to provide the title compound.

Example 2F (R)-1-(3-chloropyridin-2-yl)-3-methyl-1,2,3,6-tetrahydropyridin-4-yl trifluoromethanesulfonate (3R)-3'-chloro-3-methyl-3,6-dihydro-2H-1,2'-bipyridin-4-yl trifluoromethanesulfonate To a solution of the product from Example 2E (660 mg, 2.94 mmol) and 1,1,1-trifluoro-N-phenyl-N-(trifluoromethylsulfonyl)methanesulfonamide (1.15 g, 3.23 mmol) in tetrahydrofuran (50.0 mL) at −78° C. was added lithium bis(trimethylsilyl)amide (1.0 M in tetrahydrofuran, 3.5 mL) and the reaction mixture was stirred for 1 hour. The reaction mixture was warmed to room temperature and stirred for an additional 1 hour, concentrated, and taken up in ethyl acetate (200 mL). The organic phase was washed with saturated sodium bicarbonate, brine, dried (Na$_2$SO$_4$), and concentrated. The residue was purified by silica gel chromatography (elution with 25% ethyl acetate-hexane) to provide the title compound.

Example 2G (3S)-3'-chloro-3-methyl-N-[4-(trifluoromethyl)phenyl]-3,6-dihydro-2H-1,2'-bipyridine-4-carboxamide A solution of palladium (II) acetate (0.065 g, 0.29 mmol), the product from Example 2F (1.03 g, 2.90 mmol), triethylamine (0.293 mg, 2.90 mmol), 2-dicyclohexylphosphine-2'-(N,N-dimethylamino)biphenyl (0.228 g, 0.579 mmol) and p-trifluoromethylaniline (0.933 g, 5.79 mmol) in N,N-dimethylformamide (20 mL) was placed under 1 atmosphere of carbon monoxide and stirred at room temperature for 2 hours. The reaction mixture was concentrated to approximately, poured into of ethyl acetate, washed with saturated sodium bicarbonate, dried (Na$_2$SO$_4$), and concentrated. The residue was purified by silica gel chromatography (gradient elution from 0% to 20% ethyl acetate-[50% CH$_2$Cl$_2$-hexane] to provide the title compound. $^1$H NMR (300 MHz, CDCl$_3$) δ 8.19 (dd, 1H, J=4.7, 1.7 Hz), 7.71 (d, 2H, J=8.5 Hz), 7.62 (dd, 1H, J=7.8, 1.7 Hz), 7.60 (d, 2H, J=8.5 Hz), 6.86 (dd, 1H, J=7.8, 4.7 Hz), 6.61 (dd, 1H, J=3.1, 3.1 Hz), 4.19-3.96 (m, 2H), 3.63 (dd, 1H, J=12.5, 4.1 Hz), 3.35 (dd, 1H, J=12.5, 4.1 Hz), 3.14-3.02 (m, 1H), 1.29 (d, 3H, J=7.1 Hz); MS (DCI/NH$_3$) m/e 396 (M+H)$^+$; [α]$^{23}_D$ +37.2° (c 1.0, CH$_3$OH).

Example 3

(3S)-3,3'-dimethyl-N-{4-[(trifluoromethyl)sulfonyl]phenyl}-3,6-dihydro-2H-1,2'-bipyridine-4-carboxamide To a solution of the product from Example 1G (0.950 g, 2.066 mmol) in dioxane (20 mL) was added 1,1'-bis(diphenylphosphino)ferrocene palladium (II) chloride (0.506 g, 0.620 mmol) followed by dimethylzinc (2 M in toluene, 2.07 mL, 4.13 mmol) and the reaction stirred at room temperature for 30 minutes then at 100° C. for 1 hour. The reaction was quenched with methanol, washed with 1N HCl, dried (sodium sulfate) and concentrated in vacuo. The residue was purified by silica gel chromatography (gradient elution 0% to 20% ethyl acetate-[50% $CH_2Cl_2$-hexane]) to provide 475 mg (52%) of the title compound. $^1$H NMR (300 MHz, $CDCl_3$) δ 8.18 (dd, 1H, J=4.8, 2.0 Hz), 8.01 (d, 2H, J=8.7 Hz), 7.90 (d, 2H, J=9.1 Hz), 7.83 (br s, 1H), 7.46-7.42 (m, 1H), 6.91 (dd, 1H, J=7.1, 4.8 Hz), 6.68 (dd, 1H, J=3.6, 3.6 Hz), 3.95-3.93 (m, 2H), 3.22 (d, 2H, J=4.0 Hz), 3.12-2.98 (m, 1H), 2.35 (s, 3H), 1.27 (d, 3H, J=7.1 Hz); MS (DCI/$NH_3$) m/e 440 (M+H)$^+$; $[α]^{23}_D$ +45.0° (c 0.10, $CH_3OH$).

Example 4

(3S)-3-methyl-3'-(trifluoromethyl)-N-[4-(trifluoromethyl)phenyl]-3,6-dihydro-2H-1,2'-bipyridine-4-carboxamide

Example 4A

(2R,4R,7R)-2,4,7-trimethyl-9-(3-(trifluoromethyl)pyridin-2-yl)-1,5-dioxa-9-azaspiro[5.5]undecane The title compound (1.89 g, 75%) was prepared using similar procedure as described in Example 2D, substituting 2-chloro-3-trifluoromethylpyridine for 2,3-dichloropyridine to provide of the title compound. $^1$H NMR (300 MHz, $CDCl_3$) δ 8.38 (dd, 1H, J=4.8, 1.4 Hz), 7.82 (dd, 1H, J=7.8, 1.7 Hz), 6.93-6.89 (m, 1H), 4.12-4.01 (m, 2H), 3.44-3.34 (m, 2H), 3.21 (ddd, 1H, J=12.5, 9.5, 3.4 Hz), 3.08 (dd, 1H, J=12.6, 8.5 Hz), 2.17-2.09 (m, 1H), 2.07-2.01 (m, 1H), 1.80 (ddd, 1H, J=13.2, 9.5, 3.7 Hz), 1.70-1.50 (m, 2H), 1.22 (d, 3H, J=6.1 Hz), 1.21 (d, 3H, J=6.1 Hz), 1.00 (d, 3H, J=6.8 Hz); MS (DCI/$NH_3$) m/e 345 (M+H)$^+$.

Example 4B

(3S)-3-methyl-3'-(trifluoromethyl)-N-[4-(trifluoromethyl)phenyl]-3,6-dihydro-2H-1,2'-bipyridine-4-carboxamide The title compound (121 mg, 10%) was prepared using similar procedures as described in Examples 2E, 2F and 2G, substituting the product from Example 4A for the product from Example 2D. $^1$H NMR (300 MHz, $CDCl_3$) δ 8.48 (dd, 1H, J=4.8, 1.4 Hz), 7.93 (dd, 1H, J=7.8, 2.0 Hz), 7.71 (d, 2H, J=8.5 Hz), 7.60 (d, 2H, J=8.8 Hz), 7.05 (dd, 1H, J=7.8, 4.7 Hz), 6.57 (dd, 1H, J=3.4, 3.4 Hz), 4.10-3.88 (m, 2H), 3.47 (dd, 1H, J=12.2, 4.1 Hz), 3.30 (dd, 1H, J=12.5, 4.4 Hz), 3.13-3.00 (m, 1H), 1.20 (d, 3H, J=6.8 Hz); MS (DCI/$NH_3$) m/e 430 (M+H)$^+$; $[α]^{23}_D$ +31.6° (c 1.00, $CH_3OH$).

Example 5

(3R)-3'-chloro-3-methyl-N-{4-[(trifluoromethyl)sulfonyl]phenyl}-3,6-dihydro-2H-1,2'-bipyridine-4-carboxamide The title compound (400 mg, 52%) was prepared using similar procedures as described in Examples 1C through 1G, substituting the product from Example 2A for the product from Example 1A. $^1$H NMR (300 MHz, $CDCl_3$) δ 8.20 (d, 1H, J=4.8, 1.7 Hz), 8.02 (d, 2H, J=8.8 Hz), 7.90 (d, 2H, J=9.1 Hz), 7.77 (br s, 1H), 7.63 (dd, 1H, J=7.8, 1.7 Hz), 6.88 (dd, 1H, J=7.5, 4.8 Hz), 6.65 (dd, 1H, J=3.1, 3.1 Hz), 4.20-3.97 (m, 2H), 3.64 (dd, 1H, J=12.9, 4.1 Hz), 3.34 (dd, 1H, J=12.9, 4.4 Hz), 3.11-3.07 (m, 1H), 1.29 (d, 3H, J=6.4 Hz); MS (ESI) m/e 460 (M+H)$^+$; $[α]^{23}_D$ −30.4° (c 0.50, $CH_3OH$).

Example 6

(3R)-3,3'-dimethyl-N-{4-[(trifluoromethyl)sulfonyl]phenyl}-3,6-dihydro-2H-1,2'-bipyridine-4-carboxamide The title compound (51 mg, 54%) was prepared using similar procedure as described in Example 3, substituting the product from Example 5 for the product from Example 1G. $^1$H NMR (300 MHz, $CDCl_3$) δ 8.19-8.17 (m, 1H), 8.00 (d, 2H, J=9.2 Hz), 7.90 (d, 2H, J=9.2 Hz), 7.86 (br s, 1H), 7.47-7.43 (m, 1H), 6.91 (dd, 1H, J=7.1, 4.8 Hz), 6.68 (dd, 1H, J=3.4, 3.4 Hz), 3.94 (app t, 2H, J=2.4 Hz), 3.23 (app d, 2H, J=4.1 Hz), 3.10-2.99 (m, 1H), 2.35 (s, 3H), 1.27 (d, 3H, J=7.1 Hz); MS (DCI/$NH_3$) m/e 440 (M+H)$^+$; $[α]^{23}_D$ −38.0° (c 0.25, $CH_3OH$).

Example 7

(3R)-3'-chloro-3-methyl-N-[4-(trifluoromethyl)phenyl]-3,6-dihydro-2H-1,2'-bipyridine-4-carboxamide The title compound (340 mg, 38%) was prepared using similar procedures as described in Examples 2C through 2G, substituting (2R,4R,7S)-9-benzyl-2,4,7-trimethyl-1,5-dioxa-9-azaspiro[5.5]undecane (from Example 2A) for (2R,4R,7R)-9-benzyl-2,4,7-trimethyl-1,5-dioxa-9-azaspiro[5.5]undecane. $^1$H NMR (300 MHz, $CDCl_3$) δ 8.19 (dd, 1H, J=4.8, 1.7 Hz), 7.71 (d, 2H, J=8.5 Hz), 7.62 (dd, 1H, J=7.8, 1.7 Hz), 7.61 (d, 2H, J=8.5 Hz), 7.60 (br s, 1H), 6.86 (dd, 1H, J=7.8, 4.7 Hz), 6.61 (dd, 1H, J=3.4 Hz), 4.18-3.95 (m, 2H), 3.63 (dd, 1H, J=12.5, 4.1 Hz), 3.34 (dd, 1H, J=12.5, 4.1 Hz), 3.15-3.02 (m, 1H), 1.29 (d, 3H, J=7.1 Hz); MS (DCI/$NH_3$) m/e 396 (M+H)$^+$; $[α]^{23}_D$ −28.7° (c 0.3, $CH_3OH$).

Example 8

(3S)-3,3'-dimethyl-N-[4-(trifluoromethyl)phenyl]-3,6-dihydro-2H-1,2'-bipyridine-4-carboxamide The title compound (185 mg, 24%) was prepared using similar procedure as described in Example 3, substituting the product from Example 2G for the product from Example 1G. $^1$H NMR (300 MHz, DMSO-$d_6$) δ 10.24 (br s, 1H), 8.13 (dd, 1H, J=4.8, 1.7 Hz), 7.93 (d, 2H, J=8.5 Hz), 7.68 (d, 2H, J=8.5 Hz), 7.55-7.52 (m, 1H), 6.95 (dd, 1H, J=7.5, 5.1 Hz), 6.70 (dd, 1H, J=2.7, 2.7 Hz), 3.87-3.81 (m, 2H), 3.15-3.11 (m, 2H), 3.03-2.93 (m, 1H), 2.32 (s, 3H), 1.16 (d, 3H, J=6.8 Hz); MS (DCI/$NH_3$) m/e 376 (M+H)$^+$; $[α]^{23}_D$ +15.0° (c 0.45, $CH_3OH$).

Example 9

(3R)-3,3'-dimethyl-N-[4-(trifluoromethyl)phenyl]-3,6-dihydro-2H-1,2'-bipyridine-4-carboxamide

Example 9A 1-(3-methylpyridin-2-yl)piperidin-4-one

A mixture of 2-chloro-3-methylpyridine (5.0 mL, 45.8 mmol), $Pd_2dba_3.CHCl_3$ (0.958 g, 0.926 mmol), racemic 2,2'-bis(diphenylphosphino)-1,1'binaphthyl (1.43 g, 2.30 mmol), sodium tert-butoxide (8.51 g, 88.6 mmol), and 1,4-dioxa-8-azaspiro-[4.5]decane (5.6 mL, 44 mmol) in toluene (135 mL) was heated to 100° C. for 3.5 hours. The mixture was then diluted with ethyl acetate, washed with water and brine, dried over $Na_2SO_4$, and filtered through silica with 70% diethyl ether/hexanes to give 11.5 g of impure substituted pyridine as a red oil. This material was stirred in concentrated HCl (60 mL) for 6 hours, quenched with concentrated $NH_4OH$ (80 mL), diluted with ethyl acetate, washed with water and brine, dried ($Na_2SO_4$), filtered through silica with 80% diethyl ether/hexanes, and concentrated under reduced pressure to provide the title compound, which was used without further purification. MS ($DCI/NH_3$) m/e 191 $(M+H)^+$.

Example 9B (±)-3-Methyl-1-(3-methylpyridin-2-yl)piperidin-4-one

To a suspension of sodium hydride (1.7 g, 42 mmol) in THF (80 mL) at room temperature were added the product of Example 9A (6.65 g, 38.5 mmol) and iodomethane (2.9 ml, 46 mmol) as solution in THF (8 ml) drop wise. The mixture was stirred for 5 hours at 60° C. The reaction mixture was filtered and then concentrated under reduced pressure. The residue was partitioned between water and ethyl acetate. The organic layer was washed with brine, dried over $Na_2SO_4$, filtered and then concentrated under reduced pressure. The residue was purified via silica gel chromatography (gradient elution, 0 to 30% diethyl ether-hexanes) to provide the title compound together with a small, inseparable quantity of 3,3-dimethyl-1-(3-methylpyridin-2-yl)piperidin-4-one. MS ($DCI/NH_3$) m/e 205 $(M+H)^+$.

Example 9C (±)-3-Methyl-1-(3-methylpyridin-2-yl)-1,2,3,6-tetrahydropyridin-4-yl trifluoromethanesulfonate The title compound was prepared using similar procedure as described in Example 1F, substituting the product from Example 9B for the product from Example 1E. MS ($DCI/NH_3$) m/e 337 $(M+H)^+$.

Example 9D (±)-methyl 3,3'-dimethyl-3,6-dihydro-2H-1,2'-bipyridine-4-carboxylate To a 1:1 mixture of N,N-dimethylformamide: methanol saturated with CO, was added the product from Example 9C (5.29 g, 15.6 mmol), palladium (II) acetate (0.088 g, 0.39 mmol), triphenylphosphine (0.31 g, 1.2 mmol) and triethylamine (4.3 ml, 31 mmol). The reaction was stirred overnight at room temperature under a CO atmosphere. The mixture was then partitioned between water and ether and the organic layer was washed with brine then dried over $Na_2SO_4$, filtered, and concentrated under reduced pressure. The residue was purified via silica gel chromatography (gradient elution, 0 to 30% diethyl ether-hexanes) to provide the title compound. MS ($DCI/NH_3$) m/e 247 $(M+H)^+$.

Example 9E (±)-3,3'-dimethyl-N-[4-(trifluoromethyl)phenyl]-3,6-dihydro-2H-1,2'-bipyridine-4-carboxamide To a solution of 4-(trifluoromethyl)aniline (1.13 g, 7.00 mmol) in dichloromethane (14 mL) at room temperature was added a 2N solution of trimethylaluminum in toluene (3.50 mL, 7.00 mmol) in a dropwise fashion. The reaction was stirred for 30 minutes at room temperature under a nitrogen atmosphere. A solution of Example 9D (862 mg, 3.50 mmol) in dichloromethane (3 mL) was added and the mixture was stirred for 1 hour at room temperature under a nitrogen atmosphere. The reaction was diluted with ethyl acetate then quenched with 0.5N HCl. The organic layer was separated and then washed successively with 1N NaOH, water, and brine. The organic layer was then dried over $Na_2SO_4$, filtered, and concentrated under reduced pressure. The residue was purified via silica gel chromatography (gradient elution with 0 to 15% ethyl acetate-[50% $CH_2Cl_2$:hexanes] to provide the title compound. MS ($DCI/NH_3$) m/e 460 $(M+H)^+$.

Example 9F (3R)-3,3'-dimethyl-N-[4-(trifluoromethyl)phenyl]-3,6-dihydro-2H-1,2'-bipyridine-4-carboxamide The title compound was prepared by chiral separation of Example 9E by HPLC (Chiralcel OD column, elution with 20% (1:1 methanol:ethanol)-hexanes) at 0.7 mL/min to provide the first eluting enantiomer ((3S)-3,3'-dimethyl-N-[4-(trifluoromethyl)phenyl]-3,6-dihydro-2H-1,2'-bipyridine-4-carboxamide, retention time=10.3 min) along with the second eluting enantiomer ((3R)-3,3'-dimethyl-N-[4-(trifluoromethyl)phenyl]-3,6-dihydro-2H-1,2'-bipyridine-4-carboxamide, retention time=12.2 min). $^1H$ NMR (300 MHz, DMSO-$d_6$) δ 10.24 (br s, 1H), 8.13 (dd, 1H, J=4.8, 1.7 Hz), 7.93 (d, 2H, J=8.5 Hz), 7.68 (d, 2H, J=8.5 Hz), 7.55-7.52 (m, 1H), 6.95 (dd, 1H, J=7.1, 4.4 Hz), 6.70 (dd, 1H, J=3.0, 3.0 Hz), 3.87-3.81 (m, 2H), 3.15-3.11 (m, 2H), 3.03-2.93 (m, 1H), 2.32 (s, 3H), 1.16 (d, 3H, J=6.8 Hz); MS ($DCI/NH_3$) m/e 376 $(M+H)^+$; $[α]^{23}_D$ −25.0° (c 0.40, $CH_3OH$).

Example 10

(3R)-3-methyl-3'-(trifluoromethyl)-N-[4-(trifluoromethyl)phenyl]-3,6-dihydro-2H-1,2'-bipyridine-4-carboxamide

Example 10A 1-(3-(Trifluoromethyl)pyridin-2-yl)piperidin-4-one

The title compound was prepared using a similar procedure as described in Example 9A, substituting 2-chloro-3-(trifluoromethyl)pyridine for 2-chloro-3-methylpyridine. MS ($DCI/NH_3$) m/e 245 $(M+H)^+$.

Example 10B (±)-3-Methyl-1-(3-(trifluoromethyl)pyridin-2-yl) piperidin-4-one

The title compound was prepared using a similar procedure as described in Example 9B, substituting the product from Example 10A for the product from Example 9A. MS (DCI/NH$_3$) m/e 259 (M+H)$^+$.

Example 10C (±)-3-Methyl-1-(3-(trifluoromethyl)pyridin-2-yl)-1,2,3,6-tetrahydropyridin-4-yl trifluoromethanesulfonate The title compound was prepared using a similar procedure as described in Example 9C, substituting the product from Example 10B for the product from Example 9B. MS (DCI/NH$_3$) m/e 391 (M+H)$^+$.

Example 10D (±)-methyl 3-methyl-3'-(trifluoromethyl)-3,6-dihydro-2H-1,2'-bipyridine-4-carboxylate The title compound was prepared using a similar procedure as described in Example 9D, substituting the product from Example 10C for the product from Example 9C. MS (DCI/NH$_3$) m/e 301 (M+H)$^+$.

Example 10E (±)-3-Methyl-3'-(trifluoromethyl)-N-[4-(trifluoromethyl)phenyl]-3,6-dihydro-2H-1,2'-bipyridine-4-carboxamide The title compound was prepared using a similar procedure as described in Example 9E, substituting Example 10D for Example 9D. MS (DCI/NH$_3$) m/e 430 (M+H)$^+$.

Example 10F (3R)-3-Methyl-3'-(trifluoromethyl)-N-[4-(trifluoromethyl)phenyl]-3,6-dihydro-2H-1,2'-bipyridine-4-carboxamide The title compound was prepared by chiral separation of Example 10E by HPLC (Chiralcel OD column, elution with 20% (1:1 methanol:ethanol)-hexanes) at 0.7 mL/min to provide the first eluting enantiomer ((3S)-3-methyl-3'-(trifluoromethyl)-N-[4-(trifluoromethyl)phenyl]-3,6-dihydro-2H-1,2'-bipyridine-4-carboxamide, retention time=12.8 min) along with the second eluting enantiomer ((3R)-3-methyl-3'-(trifluoromethyl)-N-[4-(trifluoromethyl)phenyl]-3,6-dihydro-2H-1,2'-bipyridine-4-carboxamide, retention time=14.3 min). $^1$H NMR (300 MHz, DMSO-d$_6$) δ 10.25 (br s, 1H), 8.58 (dd, 1H, J=4.8, 1.0 Hz), 8.12 (dd, 1H, J=8.1, 1.7 Hz), 7.92 (d, 2H, J=8.5 Hz), 7.67 (d, 2H, J=8.8 Hz), 7.25 (dd, 1H, J=7.8, 4.8 Hz), 6.65 (dd, 1H, J=3.1, 3.1 Hz), 4.02-3.83 (m, 2H), 3.37 (dd, 1H, J=12.5, 4.4 Hz), 3.17 (dd, 1H, J=12.5, 4.8 Hz), 3.05-2.94 (m, 1H), 1.06 (d, 3H, J=7.1 Hz); MS (DCI/NH$_3$) m/e 430 (M+H)$^+$; [α]$^{23}_D$ −20.0° (c 0.40, CH$_3$OH).

Example 11

(3S)-3-methyl-1-(3-(trifluoromethyl)pyridin-2-yl)-N-(4-(trifluoromethylsulfonyl)phenyl)-1,2,3,6-tetrahydropyridine-4-carboxamide

Example 11A (±)-3-methyl-1-(3-(trifluoromethyl)pyridin-2-yl)-N-(4-(trifluoromethylsulfonyl)phenyl)-1,2,3,6-tetrahydropyridine-4-carboxamide The title compound was prepared using a similar procedure as described in Example 9E, substituting 4-[(trifluoromethyl)sulfonyl]aniline for 4-(trifluoromethyl)aniline, and substituting Example 10D for Example 9D. MS (DCI/NH$_3$) m/e 494 (M+H)$^+$.

Example 11B (3S)-3-methyl-1-(3-(trifluoromethyl)pyridin-2-yl)-N-(4-(trifluoromethylsulfonyl)phenyl)-1,2,3,6-tetrahydropyridine-4-carboxamide The title compound was prepared by chiral separation of Example 11A by HPLC (Chiralcel OD column, elution with 20% (1:1 methanol:ethanol)-hexanes) at 0.7 mL/min to provide the first eluting enantiomer (3S)-3-methyl-1-(3-(trifluoromethyl)pyridin-2-yl)-N-(4-(trifluoromethylsulfonyl)phenyl)-1,2,3,6-tetrahydropyridine-4-carboxamide, retention time=14.9 min). $^1$H NMR (300 MHz, DMSO-d$_6$) δ 10.63 (s, 1H), 8.59 (dd, J=5.5, 1.8 Hz, 1H), 8.14 (d, J=8.4 Hz, 2H), 8.12 (dd, J=8.1, 1.7 Hz, 1H), 8.08 (d, J=8.4 Hz, 2H), 7.26 (dd, J=7.5, 4.6 Hz, 1H), 6.74 (t, J=3.2 Hz, 1H), 4.03-3.84 (m, 2H), 3.37 (dd, J=12.6, 4.4 Hz, 1H), 3.17 (dd, J=12.4, 4.9 Hz, 1H), 3.02-2.96 (m, 1H), 1.07 (d, 3H); MS (DCI/NH$_3$) m/e 494 (M+H)$^+$; [α]$_D^{20}$=+28° (c 1.0, CH$_3$OH).

Example 12

(3R)-3-methyl-1-(3-(trifluoromethyl)pyridin-2-yl)-N-(4-(trifluoromethylsulfonyl)phenyl)-1,2,3,6-tetrahydropyridine-4-carboxamide The title compound was isolated as the second eluting enantiomer (retention time=17.3 min) rom the chiral separation of Example 11A by HPLC (Chiralcel OD column, elution with 20% (1:1 methanol:ethanol)-hexanes) at 0.7 mL/min. $^1$H NMR (300 MHz, DMSO-d$_6$) δ 10.63 (s, 1H), 8.59 (dd, J=5.5, 1.8 Hz, 1H), 8.14 (d, J=8.4 Hz, 2H), 8.12 (dd, J=8.1, 1.7 Hz, 1H), 8.08 (d, J=8.4 Hz, 2H), 7.26 (dd, J=7.5, 4.6 Hz, 1H), 6.74 (t, J=3.2 Hz, 1H), 4.03-3.84 (m, 2H), 3.37 (dd, J=12.6, 4.4 Hz, 1H), 3.17 (dd, J=12.4, 4.9 Hz, 1H), 3.02-2.96 (m, 1H), 1.07 (d, 3H); MS (DCI/NH$_3$) m/e 494 (M+H)$^+$; [α]$_D^{20}$=−20° (c 1.0, CH$_3$OH).

Example 13

(3S)—N-(4-(2-cyanopropan-2-yl)phenyl)-3-methyl-1-(3-(trifluoromethyl)pyridin-2-yl)-1,2,3,6-tetrahydropyridine-4-carboxamide

Example 13A (±)-N-(4-(2-cyanopropan-2-yl)phenyl)-3-methyl-1-(3-(trifluoromethyl)pyridin-2-yl)-1,2,3,6-tetrahydropyridine-4-carboxamide The title compound was prepared using a similar procedure as described in Example 9E, substituting 2-(4-aminophenyl)-

2-methylpropanenitrile for 4-(trifluoromethyl)aniline, and substituting Example 10D for Example 9D. MS (DCI/NH$_3$) m/e 429 (M+H)$^+$.

Example 13B (3S)—N-(4-(2-cyanopropan-2-yl)phenyl)-3-methyl-1-(3-(trifluoromethyl)pyridin-2-yl)-1,2,3,6-tetrahydropyridine-4-carboxamide The title compound was isolated from the chiral separation of Example 13A by HPLC (Chiralcel OD column, elution with 20% (1:1 methanol:ethanol)-hexanes) at 0.7 mL/min as the first eluting enantiomer with retention time=18.2 min). $^1$H NMR (300 MHz, DMSO-d$_6$) δ 9.97 (s, 1H), 8.57 (dd, J=5.5, 1.8 Hz, 1H), 8.11 (dd, J=8.1, 1.7 Hz, 1H), 7.74 (d, J=8.3 Hz, 2H), 7.44 (d, J=8.3 Hz, 2H), 7.24 (dd, J=7.4, 4.4 Hz, 1H), 6.59 (t, J=2.9 Hz, 1H), 3.99-3.82 (m, 2H), 3.37 (dd, 1H), 3.16 (dd, 1H), 3.02-2.96 (m, 1H), 1.67 (s, 6H), 1.05 (d, 3H); MS (DCI/NH$_3$) m/e 429 (M+H)$^+$.

Example 14

(3R)—N-(4-(2-cyanopropan-2-yl)phenyl)-3-methyl-1-(3-(trifluoromethyl)pyridin-2-yl)-1,2,3,6-tetrahydropyridine-4-carboxamide The title compound was isolated from the chiral separation of Example 13A by HPLC (Chiralcel OD column, elution with 20% (1:1 methanol:ethanol)-hexanes) at 0.7 mL/min as the second eluting enantiomer (retention time=21.0 min). $^1$H NMR (300 MHz, DMSO-d$_6$) δ 9.97 (s, 1H), 8.57 (dd, J=5.5, 1.8 Hz, 1H), 8.11 (dd, J=8.1, 1.7 Hz, 1H), 7.74 (d, J=8.3 Hz, 2H), 7.44 (d, J=8.3 Hz, 2H), 7.24 (dd, J=7.4, 4.4 Hz, 1H), 6.59 (t, J=2.9 Hz, 1H), 3.99-3.82 (m, 2H), 3.37 (dd, 1H), 3.16 (dd, 1H), 3.02-2.96 (m, 1H), 1.67 (s, 6H), 1.05 (d, 3H); MS (DCI/NH$_3$) m/e 429 (M+H)$^+$; [α]$_D^{20}$=−51° (c 0.3, CH$_3$OH).

Example 15

(3S)—N-(4-tert-butylphenyl)-3-methyl-1-(3-methylpyridin-2-yl)-1,2,3,6-tetrahydropyridine-4-carboxamide

Example 15A (±)-N-(4-tert-butylphenyl)-3-methyl-1-(3-methylpyridin-2-yl)-1,2,3,6-tetrahydropyridine-4-carboxamide The title compound was prepared using a similar procedure as described in Example 9E, substituting 4-tert-butylaniline for 4-(trifluoromethyl)aniline. MS (DCI/NH$_3$) m/e 364 (M+H)$^+$.

Example 15B (3S)—N-(4-tert-butylphenyl)-3-methyl-1-(3-methylpyridin-2-yl)-1,2,3,6-tetrahydropyridine-4-carboxamide The title compound was isolated as the first eluting enantiomer (retention time=11.6 min) from the chiral separation of Example 15A by HPLC (Chiralcel OD column, elution with 20% (1:1 methanol:ethanol)-hexanes) at 0.7 mL/min. $^1$H NMR (300 MHz, DMSO-d$_6$) δ 9.80 (s, 1H), 8.13 (dd, J=6.2, 1.7 Hz, 1H), 7.61 (d, J=8.0 Hz, 2H), 7.53 (dd, J=8.1, 1.8 Hz, 1H), 7.31 (d, J=8.3 Hz, 2H), 6.95 (dd, J=7.1, 4.0 Hz, 1H), 6.60 (t, J=3.2 Hz, 1H), 3.83-3.79 (m, 2H), 3.12 (d, J=1.9 Hz, 2H), 3.00-2.94 (m, 1H), 2.31 (s, 3H), 1.27 (s, 9H), 1.15 (d, 3H); MS (DCI/NH$_3$) m/e 364 (M+H)$^+$; [α]$_D^{20}$=+40° (c 1.0, CH$_3$OH).

Example 16

(3R)—N-(4-tert-butylphenyl)-3-methyl-1-(3-methylpyridin-2-yl)-1,2,3,6-tetrahydropyridine-4-carboxamide The title compound was isolated as the second eluting enantiomer (retention time=14.4 min) from the chiral separation of Example 15A by HPLC (Chiralcel OD column, elution with 20% (1:1 methanol:ethanol)-hexanes) at 0.7 mL/min. $^1$H NMR (300 MHz, DMSO-d$_6$) δ 9.80 (s, 1H), 8.13 (dd, J=6.2, 1.7 Hz, 1H), 7.61 (d, J=8.0 Hz, 2H), 7.53 (dd, J=8.1, 1.8 Hz, 1H), 7.31 (d, J=8.3 Hz, 2H), 6.95 (dd, J=7.1, 4.0 Hz, 1H), 6.60 (t, J=3.2 Hz, 1H), 3.83-3.79 (m, 2H), 3.12 (d, J=1.9 Hz, 2H), 3.00-2.94 (m, 1H), 2.31 (s, 3H), 1.27 (s, 9H), 1.15 (d, 3H); MS (DCI/NH$_3$) m/e 364 (M+H)$^+$; [α]$_D^{20}$=−40° (c 1.0, CH$_3$OH).

Example 17

(3S)—N-(4-(2-cyanopropan-2-yl)phenyl)-3-methyl-1-(3-methylpyridin-2-yl)-1,2,3,6-tetrahydropyridine-4-carboxamide

Example 17A (±)-N-(4-(2-cyanopropan-2-yl)phenyl)-3-methyl-1-(3-methylpyridin-2-yl)-1,2,3,6-tetrahydropyridine-4-carboxamide The title compound was prepared using a similar procedure as described in Example 9E, substituting 2-(4-aminophenyl)-2-methylpropanenitrile for 4-(trifluoromethyl)aniline. MS (DCI/NH$_3$) m/e 375 (M+H)$^+$.

Example 17B (3S)—N-(4-(2-cyanopropan-2-yl)phenyl)-3-methyl-1-(3-methylpyridin-2-yl)-1,2,3,6-tetrahydropyridine-4-carboxamide The title compound was isolated as the first eluting enantiomer (retention time=16.1 min) from the chiral separation of Example 17A by HPLC (Chiralcel OD column, elution with 20% (1:1 methanol:ethanol)-hexanes) at 0.7 mL/min. $^1$H NMR (300 MHz, DMSO-d$_6$) δ 9.96 (s, 1H), 8.13 (dd, J=6.2, 1.7 Hz, 1H), 7.74 (d, J=8.1 Hz, 2H), 7.53 (dd, J=8.2, 2.0 Hz, 1H), 7.45 (d, J=8.1 Hz, 2H), 6.95 (dd, J=7.2, 3.9 Hz, 1H), 6.64 (t, J=3.3 Hz, 1H), 3.85-3.81 (m, 2H), 3.12 (d, J=2.0 Hz, 2H), 3.00-2.94 (m, 1H), 2.31 (s, 3H), 1.67 (s, 6H), 1.16 (d, 3H); MS (DCI/NH$_3$) m/e 375 (M+H)$^+$; [α]$_D^{20}$=+33° (c 1.0, CH$_3$OH).

Example 18

(3R)—N-(4-(2-cyanopropan-2-yl)phenyl)-3-methyl-1-(3-methylpyridin-2-yl)-1,2,3,6-tetrahydropyridine-4-carboxamide The title compound was isolated as the second enantiomer (retention time=19.0 min) from the chiral separation of Example 17A by HPLC (Chiralcel OD column, elution with 20% (1:1 methanol:ethanol)-hexanes) at 0.7 mL/min. $^1$H NMR (300 MHz, DMSO-$d_6$) δ 9.96 (s, 1H), 8.13 (dd, J=6.2, 1.7 Hz, 1H), 7.74 (d, J=8.1 Hz, 2H), 7.53 (dd, J=8.2, 2.0 Hz, 1H), 7.45 (d, J=8.1 Hz, 2H), 6.95 (dd, J=7.2, 3.9 Hz, 1H), 6.64 (t, J=3.3 Hz, 1H), 3.85-3.81 (m, 2H), 3.12 (d, J=2.0 Hz, 2H), 3.00-2.94 (m, 1H), 2.31 (s, 3H), 1.67 (s, 6H), 1.16 (d, 3H); MS (DCI/$NH_3$) m/e 375 (M+H)$^+$; $[α]_D^{20}$=−25° (c 0.3, $CH_3OH$).

Example 19

(3S)-3-methyl-1-(3-methylpyridin-2-yl)-N-(6-(trifluoromethyl)pyridin-3-yl)-1,2,3,6-tetrahydropyridine-4-carboxamide Example 19A (±)-3-methyl-1-(3-methylpyridin-2-yl)-N-(6-(trifluoromethyl)pyridin-3-yl)-1,2,3,6-tetrahydropyridine-4-carboxamide The title compound was prepared using a similar procedure as described in Example 9E, substituting 6-(trifluoromethyl)pyridin-3-amine for 4-(trifluoromethyl)aniline. MS (DCI/$NH_3$) m/e 377 (M+H)$^+$.

Example 19B (3S)-3-methyl-1-(3-methylpyridin-2-yl)-N-(6-(trifluoromethyl)pyridin-3-yl)-1,2,3,6-tetrahydropyridine-4-carboxamide The title compound was isolated as the first eluting enantiomer (retention time=16.8 min) from the chiral separation of Example 19A by HPLC (Chiralcel OD column, elution with 20% (1:1 methanol:ethanol)-hexanes) at 0.7 mL/min. $^1$H NMR (300 MHz, DMSO-$d_6$) δ 10.47 (s, 1H), 9.01 (d, J=3.3 Hz, 1H), 8.41 (dd, J=8.3, 2.9 Hz, 1H), 8.14 (dd, J=4.9, 1.7 Hz, 1H), 7.87 (d, J=8.8 Hz, 1H), 7.56-7.52 (m, 1H), 6.96 (dd, J=8.5, 4.31H), 6.78 (t, J=3.4 Hz, 1H), 3.87-3.85 (m, 2H), 3.14 (dd, J=7.9, 3.3 Hz, 2H), 3.02-2.94 (m, 1H), 2.32, (s, 3H), 1.18 (d, J=7.8 Hz, 3H); MS (DCI/$NH_3$) m/e 377 (M+H)$^+$; $[α]_D^{20}$=+20° (c 0.4, $CH_3OH$).

Example 20

(3R)-3-methyl-1-(3-methylpyridin-2-yl)-N-(6-(trifluoromethyl)pyridin-3-yl)-1,2,3,6-tetrahydropyridine-4-carboxamide The title compound was isolated as the second eluting isomer (retention time=18.4 min) from the chiral separation of Example 19A by HPLC (Chiralcel OD column, elution with 20% (1:1 methanol:ethanol)-hexanes) at 0.7 mL/min. $^1$H NMR (300 MHz, DMSO-$d_6$) δ 10.47 (s, 1H), 9.01 (d, J=3.3 Hz, 1H), 8.41 (dd, J=8.3, 2.9 Hz, 1H), 8.14 (dd, J=4.9, 1.7 Hz, 1H), 7.87 (d, J=8.8 Hz, 1H), 7.56-7.52 (m, 1H), 6.96 (dd, J=8.5, 4.31H), 6.78 (t, J=3.4 Hz, 1H), 3.87-3.85 (m, 2H), 3.14 (dd, J=7.9, 3.3 Hz, 2H), 3.02-2.94 (m, 1H), 2.32, (s, 3H), 1.18 (d, J=7.8 Hz, 3H); MS (DCI/$NH_3$) m/e 377 (M+H)$^+$; $[α]_D^{20}$=−26° (c 0.4, $CH_3OH$).

e) BIOLOGICAL DATA

In Vitro Data—Determination of Inhibition Potencies

Dulbecco's modified Eagle medium (D-MEM) (with 4.5 mg/mL glucose) and fetal bovine serum were obtained from Hyclone Laboratories, Inc. (Logan, Utah). Dulbecco's phosphate-buffered saline (D-PBS) (with 1 mg/mL glucose and 3.6 mg/l Na pyruvate, without phenol red), L-glutamine, hygromycin B, and Lipofectamine® were obtained from Life Technologies (Grand Island, N.Y.). G418 sulfate was obtained from Calbiochem-Novabiochem Corp. (San Diego, Calif.). Capsaicin (8-methyl-N-vanillyl-6-nonenamide) was obtained from Sigma-Aldrich, Co. (St. Louis, Mo.). Fluo-4 AM (N-[4-[6-[(acetyloxy)methoxy]-2,7-difluoro-3-oxo-3H-xanthen-9-yl]-2-[2-[2-[bis[2-[(acetyloxy)methoxy]-2-oxyethyl]amino]-5-methylphenoxy]ethoxy]phenyl]-N-[2-[(acetyloxy)methoxy]-2-oxyethyl]-glycine, (acetyloxy) methyl ester) was purchased from Molecular Probes (Eugene, Oreg.).

The cDNAs for the human TRPV1 receptor were isolated by reverse transcriptase-polymerase chain reaction (RT-PCR) from human small intestine poly A+RNA supplied by Clontech (Palo Alto, Calif.) using primers designed surrounding the initiation and termination codons identical to the published sequences (Hayes et al. Pain 2000, 88, 205-215). The resulting cDNA PCR products were subcloned into pCIneo mammalian expression vector (Promega) and fully sequenced using fluorescent dye-terminator reagents (Prism, Perkin-Elmer Applied Biosystems Division) and a Perkin-Elmer Applied Biosystems Model 373 DNA sequencer or Model 310 genetic analyzer. Expression plasmids encoding the hTRPV1 cDNA were transfected individually into 1321N1 human astrocytoma cells using Lipofectamine®. Forty-eight hours after transfection, the neomycin-resistant cells were selected with growth medium containing 800 μg/mL Geneticin (Gibco BRL). Surviving individual colonies were isolated and screened for TRPV1 receptor activity. Cells expressing recombinant homomeric TRPV1 receptors were maintained at 37° C. in D-MEM containing 4 mM L-glutamine, 300 μg/mL G418 (Cal-biochem) and 10% fetal bovine serum under a humidified 5% $CO_2$ atmosphere.

The functional activity of compounds at the TRPV1 receptor was determined with a $Ca^{2+}$ influx assay and measurement of intracellular $Ca^{2+}$ levels ($[Ca^{2+}]_i$). All compounds were tested over an 11-point half-log concentration range. Compound solutions were prepared in D-PBS (4× final concentration), and diluted serially across 96-well v-bottom tissue culture plates using a Biomek 2000 robotic automation workstation (Beckman-Coulter, Inc., Fullerton, Calif.). A 0.2 μM solution of the TRPV1 agonist capsaicin was also prepared in D-PBS. The fluorescent $Ca^{2+}$ chelating dye Fluo-4 AM was used as an indicator of the relative levels of $[Ca^{2+}]_i$ in a 96-well format using a Fluorescence Imaging Plate Reader (FLIPR) (Molecular Devices, Sunnyvale, Calif.). Cells were grown to confluency in 96-well black-walled tissue culture plates. Then, prior to the assay, the cells were loaded with 100 μL per well of Fluo-4 AM (2 μM, in D-PBS) for 1-2 hours at 23° C. Washing of the cells was performed to remove extracellular Fluo-4 AM (2×1 mL D-PBS per well), and afterward, the cells were placed in the reading chamber of the FLIPR instrument. 50 μL of the compound solutions were added to the cells at the 10 second time mark of the experimental run. Then, after a 3-minute time delay, 50 μL of the capsaicin solution was added at the, 190 second time mark (0.05 μM final concentration)(final volume=200 μL) to challenge the TRPV1 receptor. Time length of the experimental run was 240 seconds. Fluorescence readings were made at 1 to 5 second intervals over the course of the experimental run. The peak increase in relative fluorescence units (minus baseline) was calculated from the 190 second time mark to the end of the experimental run, and expressed as a percentage of the 0.05 μM capsaicin (control) response. Curve-fits of the data were solved using a four-parameter logistic Hill equation in Graph Pad Prism® (GraphPad Software, Inc., San Diego, Calif.), and $IC_{50}$ values were calculated.

The compounds of the examples were tested in the assay described above. Representative (3S)-enantiomers of the present invention have $IC_{50}$ of about 20 nM to about 200 nM, and are more potent than their corresponding (3R)-enantiomers, as shown in Table I.

TABLE I

| Example | Stereoisomer | hTRPV1 $IC_{50}$ (nM) |
|---|---|---|
| 1 | (S) | 28 |
| 5 | (R) | 230 |
| 2 | (S) | 20 |
| 7 | (R) | 84 |
| 3 | (S) | 20 |
| 6 | (R) | 760 |
| 4 | (S) | 26 |
| 10 | (R) | 480 |
| 8 | (S) | 63 |
| 9 | (R) | 380 |
| 11 | (S) | 40 |
| 12 | (R) | 640 |
| 13 | (S) | 89 |
| 14 | (R) | 710 |
| 15 | (S) | 15 |
| 16 | (R) | 620 |
| 17 | (S) | 13 |
| 18 | (R) | 1300 |
| 19 | (S) | 190 |
| 20 | (R) | 3100 |

The in vitro data demonstrates that (3S)-enantiomers of the present invention more effectively antagonize the TRPV1 receptor than the corresponding (3R)-enantiomers. The unexpected improvement in the effectiveness of the (3 S)-enantiomers of the present invention makes these compounds a better choice as therapeutic agents. This interesting property may result in better dosage quantities of the TRPV 1 antagonists with which the same beneficial therapeutic effects can be induced, either without or with diminished unwanted side effects. Compounds of the present invention include but are not limited to:

(3S)-3'-chloro-3-methyl-N-{4-[(trifluoromethyl)sulfonyl]phenyl}-3,6-dihydro-2H-1,2'-bipyridine-4-carboxamide;

(3S)-3'-chloro-3-methyl-N-[4-(trifluoromethyl)phenyl]-3,6-dihydro-2H-1,2'-bipyridine-4-carboxamide;

(3S)-3,3'-dimethyl-N-{4-[(trifluoromethyl)sulfonyl]phenyl}-3,6-dihydro-2H-1,2'-bipyridine-4-carboxamide;

(3S)-3-methyl-3'-(trifluoromethyl)-N-[4-(trifluoromethyl)phenyl]-3,6-dihydro-2H-1,2'-bipyridine-4-carboxamide;

(3S)-3,3'-dimethyl-N-[4-(trifluoromethyl)phenyl]-3,6-dihydro-2H-1,2'-bipyridine-4-carboxamide;

(3S)-3-methyl-1-(3-(trifluoromethyl)pyridin-2-yl)-N-(4-(trifluoromethylsulfonyl)phenyl)-1,2,3,6-tetrahydropyridine-4-carboxamide;

(3S)—N-(4-(2-cyanopropan-2-yl)phenyl)-3-methyl-1-(3-(trifluoromethyl)pyridin-2-yl)-1,2,3,6-tetrahydropyridine-4-carboxamide;

(3S)—N-(4-tert-butylphenyl)-3-methyl-1-(3-methylpyridin-2-yl)-1,2,3,6-tetrahydropyridine-4-carboxamide;

(3S)—N-(4-(2-cyanopropan-2-yl)phenyl)-3-methyl-1-(3-methylpyridin-2-yl)-1,2,3,6-tetrahydropyridine-4-carboxamide;

(3S)-3-methyl-1-(3-methylpyridin-2-yl)-N-(6-(trifluoromethyl)pyridin-3-yl)-1,2,3,6-tetrahydropyridine-4-carboxamide;

or a pharmaceutically acceptable salt thereof.

Compounds of the present invention, including but not limited to those specified in the examples, can be used to treat pain as demonstrated by Nolano, M. et al., Pain 1999, 81, 135-145; Caterina, M. J. and Julius, D., Annu. Rev. Neurosci., 2001, 24, 487-517; Caterina, M. J. et al., Science, 2000, 288, 306-313; Caterina, M. J. et al., Nature, 1997, 389, 816-824.

Physiological pain is an important protective mechanism designed to warn of danger from potentially injurious stimuli from the external environment. The system operates through a specific set of primary sensory neurons and is activated by noxious stimuli via peripheral transducing mechanisms (see Millan, Prog. Neurobiol., 1999, 57, 1-164 for a review). These sensory fibers are known as nociceptors and are characteristically small-diameter axons with slow conduction velocities. Nociceptors encode the intensity, duration and quality of noxious stimulus and by virtue of their topographically organized projection to the spinal cord, the location of the stimulus. The nociceptors are found on nociceptive nerve fibers of which there are two main types, A-delta fibers (myelinated) and C fibers (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitization in the periphery, locally around the injury and centrally where the nociceptors terminate. These effects lead to a heightened sensation of pain. In acute pain, these mechanisms can be useful in promoting protective behaviors that may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibers associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia: Meyer et al., Textbook of Pain, 13-44 (1994)). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury.

Pain afferents are activated by transduction of stimuli by nociceptors at the site of injury and activate neurons in the spinal cord at the level of their termination. This is then relayed up the spinal tracts to the brain where pain is perceived (Meyer et al., Textbook of Pain, 13-44 (1994). The activation of nociceptors activates two types of afferent nerve fibers. Myelinated A-delta fibers transmit rapidly and are responsible for sharp and stabbing pain sensations, whilst unmyelinated C fibers transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumor related pain (e. g. bone pain, headache, facial pain or visceral pain) or pain associated with cancer therapy (e.g. post-chemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition, which can be particularly debilitating.

Neuropathic pain is currently defined as pain initiated or caused by a primary lesion or dysfunction in the nervous system. Nerve damage can be caused by trauma and disease and thus the term neuropathic pain' encompasses many disorders with diverse etiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological, as it has no protective role. It is often present well after the original cause has dissipated, commonly lasting for years, significantly decreasing a patient's quality of life (Woolf and Mannion, Lancet, 1999, 353, 1959-1964). The symptoms of neuropathic pain are difficult to treat, as they are often heterogeneous even between patients with the same disease (Woolf & Decosterd, Pain Supp., 1999, 6, S141-S147; Woolf and Mannion, Lancet, 1999, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, Textbook of Pain, 45-56 (1994)). Arthritic pain is the most common inflammatory pain.

Rheumatoid disease is one of the commonest chronic inflammatory conditions in developed countries and rheumatoid arthritis is a common cause of disability. The exact etiology of rheumatoid arthritis is unknown, but current hypotheses suggest that both genetic and microbiological factors may be important (Grennan & Jayson, Textbook of Pain, 397-407 (1994)). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, Ann Pharmacother., 2002, 36, 679-686; McCarthy et al., Textbook of Pain, 387-395 (1994)). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs. Fernihough, J. et al. describe in Neuroscience Letters, 2005, 75-80 a potential role for TRPV1 in the manifestation of pain behavior accompanied by osteoarthritis changes in the knee.

Compounds of the invention as TRPV1 antagonists are useful in ameliorating acute and chronic inflammatory pain and postoperative pain as demonstrated in Honore, P. et al., The Journal of Pharmacology and Experimental Therapeutics, 2005, 410-421.

Another type of inflammatory pain is visceral pain, which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain.

Commonly encountered gastrointestinal (GI) disorders that cause pain include functional bowel disorder (FBD) and inflammatory bowel disease (IBD). These GI disorders include a wide range of disease states that are currently only moderately controlled, including, with respect to FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Elevated TRPV1 immunoreactivity has been observed in colonic sensory nerve fibers in patients with IBD (Szallasi, A., et al. Nature Reviews, 2007, 6, 357-373).

Other types of visceral pain include the pain associated with dysmenorrhea, cystitis and pancreatitis and pelvic pain.

It should be noted that some types of pain have multiple etiologies and thus can be classified in more than one area, e.g. back pain and cancer pain have both nociceptive and neuropathic components.

Other types of pain include: pain resulting from musculoskeletal disorders, including myalgia, fibromyalgia, spondylitis, sero-negative (non-rheumatoid) arthropathies, non-articular rheumatism, dystrophinopathy, glycogenolysis, polymyositis and pyomyositis; heart and vascular pain, including pain caused by angina, myocardical infarction, mitral stenosis, pericarditis, Raynaud's phenomenon, scleredoma and skeletal muscle ischemia; head pain, such as migraine (including migraine with aura and migraine without aura), cluster headache, tension-type headache mixed headache and headache associated with vascular disorders; and orofacial pain, including dental pain, otic pain, burning mouth syndrome and temporomandibular myofascial pain. It has been shown that CGRP-receptor antagonists block the vasodilation effects of CGRP and exhibits efficacy in patients with migraine and cluster headaches. CGRP is strongly coexpressed in many TRPV1 expressing nerve fibers, it is plausible that activation of TRPV1 could partially underlie a neurogenic-mediated component of headache.

It is known that capsaicin, a TRPV1 agonist, induces cough and reduced airway conductance in human clinical trials. TRPV1 antagonists such as capsazepine have been shown to block capsaicin and citric acid-induced cough responses in guinea pigs as demonstrated by Geppetti, P. et al, European Journal of Pharmacology, 2006, 533, 207-214. Thus, TRPV1 antagonists demonstrate potential in the treatment of asthma, cough, chronic obstructive pulmonary disease (COPD) and bronchoconstriction as demonstrated by Watanabe, N. et al, Pulmonary Pharmacology and Therapeutics, 2005, 18, 187-197 and Jia, Y. et al, British Journal of Pharmacology, 2002, 137, 831-836.

Compounds of the present invention, including but not limited to those specified in the examples, can be used to treat bladder overactivity and/or urinary incontinence as demonstrated by Fowler, C. Urology 2002, 55, 60-64.

Compounds of the present invention, including but not limited to those specified in the examples, can be used to treat inflammatory thermal hyperalgesia as demonstrated by Davis, J. et al., Nature, 2000, 405, 183-187.

Compounds of the present invention, including but not limited to those specified in the examples, can be used as for the treatment of anxiety-related disorders as demonstrated by Marsch, R. et al., Journal of Neuroscience 2007, 27, 832-839.

Compounds of the present invention, including but not limited to those specified in the examples, can be used as for the treatment of disorders associated with hyperdopaminergia such as psychosis, attention deficit hyperactivity disorder and schizophrenia as demonstrated by Tzavara, E. et al., Biological Psychiatry 2006, 59, 508-515.

Compounds of the present invention, including but not limited to those specified in the examples, can be used as for the treatment of diabetes and obesity as demonstrated by Suni, A. and Sallazi, A., Trends in Pharmacological Sciences 2008, 29, 29-36.

Compounds of the invention may be administered alone, or in combination with one or more other compounds of the invention, or in combination (i.e. co-administered) with one or more additional pharmaceutical agents. For example, a compound of formula (I) or (II), or a pharmaceutically acceptable salt or solvate thereof, may be administered in combination with acetaminophen, or with one or more nonsteroidal anti-inflammatory drug (NSAID) such as, but not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments of the invention, the nonsteroidal anti-inflammatory drug (NSAID) is ibuprofen. Combination therapy includes administration of a single pharmaceutical dosage formulation containing one or more of the compounds of invention and one or more additional pharmaceutical agents, as well as administration of the compounds of the invention and each additional pharmaceutical agent, in its own separate pharmaceutical dosage formulation. For example, a compound of formula (I) and one or more additional pharmaceutical agents, may be administered to the patient together, in a single oral dosage composition having a fixed ratio of each active ingredient, such as a tablet or capsule; or each agent may be administered in separate oral dosage formulations.

Where separate dosage formulations are used, compounds of the invention and one or more additional pharmaceutical agents may be administered at essentially the same time (e.g., concurrently) or at separately staggered times (e.g., sequentially).

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salts thereof. Compounds of the invention can also be administered as a pharmaceutical composition comprising the compounds of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.10 µg/kg body weight to about 10 mg/kg body weight. More preferable doses can be in the range of from about 0.10 µg/kg body weight to about 1 mg/kg body weight. If desired, the effective daily dose can be divided into multiple doses for purposes of administration. Consequently, single dose compositions may contain such amounts or submultiples thereof to make up the daily dose.

f) PHARMACEUTICAL COMPOSITIONS

The invention also provides pharmaceutical compositions comprising of compounds of the invention, or pharmaceutically acceptable salts or solvates thereof, formulated together with one or more pharmaceutically acceptable carriers. The pharmaceutical compositions can be formulated for oral administration in solid or liquid form, for parenteral injection or for rectal administration.

The compounds identified by the methods described herein may be administered as the sole pharmaceutical agent or in combination with one or more other pharmaceutical agents where the combination causes no unacceptable adverse effects. For example, the compounds of this invention can be combined with an atypical antipsychotic. Specific examples of suitable atypical antipsychotics include, but are not limited to, clozapine, risperidone, olanzapine, quietapine, ziprasidone, zotepine, iloperidone, and the like. Thus, the present invention also includes pharmaceutical compositions which are comprised of therapeutically effective amount of compounds identified by the methods described herein, or pharmaceutically acceptable salts thereof, one or more pharmaceutical agents as disclosed hereinabove, and one or more pharmaceutically acceptable carriers.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., p 33 et seq (1976).

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds of the invention can be used in the form of pharmaceutically acceptable salts derived from inorganic or organic acids. The term "pharmaceutically acceptable salts" as used herein, include salts and zwitterions of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by mixing together solutions of the compounds of invention and a suitable acid or base. The salt may precipitate from the solution and be collected by filtration or may be recovered by evaporation of the solvent. The degree of ionization in the salt may vary from completely ionized to almost non-ionized.

Suitable acid addition salts are formed from acids which form non-toxic salts. Representative acid addition salts include, but are not limited to acetate, adipate, alginate, citrate, aspartate, benzoate, benzenesulfonate, bisulfate, bicarbonate, butyrate, camphorate, camphorsulfonate, carbonate, citrate, digluconate, glycerophosphate, hemisulfate, heptanoate, hexanoate, formate, fumarate, gluconate, glucuronate, glutamate, hydrochloride, hydrobromide, hydroiodide, 2-hydroxyethansulfonate (isethionate), lactate, maleate, malate, malonate, methanesulfonate, nicotinate, 2-naphthalenesulfonate, nicotinate, nitrate, orotate, oxalate, palmitate, pamoate, pectinate, persulfate, 3-phenylpropionate, picrate, pivalate, propionate, saccharate, stearate, succinate, sulfate, tartrate, thiocyanate, phosphate, hydrogenphosphate, dihydrogen phosphate, p-toluenesulfonate, trifluoroacetate, and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, zinc, and aluminum salts, and the like, and nontoxic quaternary ammonia and amine cations including ammonium, tetramethylammonium, tetraethylammonium, methylamine, dimethylamine, trimethylamine, triethylamine, diethylamine, and ethylamine. Other representative organic amines useful for the formation of base addition salts include ethylenediamine, ethanolamine, diethanolamine, piperidine, and piperazine.

The term "pharmaceutically acceptable prodrug" or "prodrug" as used herein, represents those prodrugs of the compounds of the invention which are, within the scope of sound medical judgment, suitable for use in contact with the tissues of humans and animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention also contemplates pharmaceutically acceptable compounds that when administered to a patient in need thereof may be converted through in vivo biotransformation into compounds of the invention.

The compounds of the invention may exist in both unsolvated and solvated forms. The term "solvate" is used herein to describe a molecular complex comprising the compound of the invention and one or more pharmaceutically acceptable solvent molecules, for example, ethanol. The term "hydrate" is employed when said solvent is water.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound selected from the group consisting of
   (3S)-3'-chloro-3-methyl-N-{4-[(trifluoromethyl)sulfonyl]phenyl}-3,6-dihydro-2H-1,2'-bipyridine-4-carboxamide;
   (3S)-3,3'-dimethyl-N-{4-[(trifluoromethyl)sulfonyl]phenyl}-3,6-dihydro-2H-1,2'-bipyridine-4-carboxamide;
   (3S)-3-methyl-3'-(trifluoromethyl)-N-[4-(trifluoromethyl)phenyl]-3,6-dihydro-2H-1,2'-bipyridine-4-carboxamide;
   (3S)-3,3'-dimethyl-N-[4-(trifluoromethyl)phenyl]-3,6-dihydro-2H-1,2'-bipyridine-4-carboxamide;
   (3S)-3-methyl-1-(3-(trifluoromethyl)pyridin-2-yl)-N-(4-(trifluoromethylsulfonyl)phenyl)-1,2,3,6-tetrahydropyridine-4-carboxamide;
   (3S)—N-(4-(2-cyano-propan-2-yl)phenyl)-3-methyl-1-(3-(trifluoromethyl)pyridin-2-yl)-1,2,3,6-tetrahydropyridine-4-carboxamide;
   (3S)—N-(4-tert-butylphenyl)-3-methyl-1-(3-methylpyridin-2-yl)-1,2,3,6-tetrahydropyridine-4-carboxamide;
   (3S)—N-(4-(2-cyanopropan-2-yl)phenyl)-3-methyl-1-(3-methylpyridin-2-yl)-1,2,3,6-tetrahydropyridine-4-carboxamide; and
   (3S)-3-methyl-1-(3-methylpyridin-2-yl)-N-(6-(trifluoromethyl)pyridin-3-yl)-1,2,3,6-tetrahydropyridine-4-carboxamide
   or a pharmaceutically acceptable salt thereof.

2. A pharmaceutical composition comprising a compound according to claim 1 or a pharmaceutically acceptable salt thereof, and one or more pharmaceutically acceptable carriers.

3. The pharmaceutical composition according to claim 2 further comprising acetaminophen or one or more nonsteroidal anti-inflammatory drug, or a combination thereof.

4. A method of treating pain, comprising administering a therapeutically effective amount of a compound according to claim 1, or a pharmaceutically acceptable salt thereof, to a subject in need thereof.

5. The method according to claim 4 further comprising the step of co-administering with acetaminophen or with one or more nonsteroidal anti-inflammatory drug, or combination thereof.

6. The method according to claim 5 wherein the nonsteroidal anti-inflammatory drug is ibuprofen.

* * * * *